United States Patent
Shtrom

(10) Patent No.: US 11,235,784 B2
(45) Date of Patent: Feb. 1, 2022

(54) SELECTIVE CONTROL TRANSITION BASED ON SITUATIONAL AWARENESS

(71) Applicant: Augmented Radar Imaging, Inc., Los Altos, CA (US)

(72) Inventor: Victor Shtrom, Los Altos, CA (US)

(73) Assignee: Augmented Radar Imaging, Inc., Los Altos, CA (US)

(*) Notice: Subject to any disclaimer, the term of this patent is extended or adjusted under 35 U.S.C. 154(b) by 181 days.

(21) Appl. No.: 16/599,124

(22) Filed: Oct. 11, 2019

(65) Prior Publication Data

US 2021/0107504 A1   Apr. 15, 2021

(51) Int. Cl.
| | |
|---|---|
| *B60W 50/14* | (2020.01) |
| *B60W 40/08* | (2012.01) |
| *A61B 5/16* | (2006.01) |
| *A61B 5/18* | (2006.01) |
| *A61B 5/00* | (2006.01) |
| *B60W 50/00* | (2006.01) |

(52) U.S. Cl.
CPC ............ *B60W 50/14* (2013.01); *A61B 5/002* (2013.01); *A61B 5/165* (2013.01); *A61B 5/18* (2013.01); *A61B 5/6893* (2013.01); *B60W 40/08* (2013.01); *B60W 2040/0818* (2013.01); *B60W 2040/0827* (2013.01); *B60W 2040/0872* (2013.01); *B60W 2050/0072* (2013.01); *B60W 2540/22* (2013.01); *B60W 2540/26* (2013.01)

(58) Field of Classification Search
CPC combination set(s) only.
See application file for complete search history.

(56) References Cited

U.S. PATENT DOCUMENTS

| | | | |
|---|---|---|---|
| 6,226,570 B1* | 5/2001 | Hahn | B60K 28/066 701/1 |
| 2014/0309870 A1* | 10/2014 | Ricci | A61B 5/6808 701/36 |
| 2015/0070160 A1* | 3/2015 | Davidsson | G05D 1/0061 340/457 |
| 2017/0206464 A1* | 7/2017 | Clayton | G06N 3/0445 |

\* cited by examiner

*Primary Examiner* — Thomas S McCormack
(74) *Attorney, Agent, or Firm* — Steven Stupp

(57) ABSTRACT

An electronic device that selectively provides a recommendation is described. During operation, the electronic device may acquire, using one or more sensors, a measurement within an environment that is external to the electronic device, where the measurement provides information associated with a person located in a driver's position or seat in a vehicle, and the measurement includes a non-contact measurement. Then, the electronic device may assess situational awareness of the person based at least in part on the measurement. Moreover, the electronic device may receive a request associated with a partial or fully autonomous vehicle application to transition to manual control of the vehicle. In response to the request, the electronic device may selectively provide the recommendation to the partial or fully autonomous vehicle application to transition to manual control of the vehicle based at least in part on the situational awareness.

20 Claims, 15 Drawing Sheets

SELECTIVE CONTROL TRANSITION BASED ON SITUATIONAL AWARENESS

BACKGROUND

Field

The described embodiments relate to an electronic device that acquires a non-contact measurement in or of an environment that includes the electronic device, and then selectively performs a predefined action based at least in part on the measurement.

Related Art

Self-driving (which is sometimes referred to as 'autonomous driving') is an emerging technology that is expected to revolutionize the automotive and trucking industries, as well as mass transit. In addition, self-driving or autonomous vehicles can enable new products and services, such as ride-sharing services. Consequently, self-driving is a disruptive technology that, if brought to fruition, can impact a significant fraction of the national economy.

An autonomous vehicle typically uses a sensor technology to monitor a surrounding environment, so that the autonomous vehicle can navigate with limited or without human input. For example, the sensor technology may include laser light, such as light detection and ranging (lidar). Then, advanced control systems in the autonomous vehicle may analyze this sensor information to identify signs and obstacles (such as pedestrians, bicyclists and/or other cars), and to appropriately navigate the autonomous vehicle.

However, there are obstacles to the adoption of self-driving technology. Notably, even well-trained self-driving technology can encounter a novel or unexpected circumstance or a driving condition that exceeds the capabilities of the self-driving technology. Typically, when this occurs, the self-driving technology often disengages, returning a vehicle to manual control.

Unfortunately, this transition is typically problematic and can be dangerous. Notably, the 'driver' of the vehicle is often unprepared or unable to assume effective control of the vehicle. For example, even if the driver's hands are on the steering wheel, that does not mean that the driver is ready to drive the vehicle, especially on short notice or in an adverse situation. Consequently, when self-driving technology suddenly disengages, the driver may be unable to avoid an accident. Therefore, preventive disengagement of self-driving technology is currently often ineffective as a safety mechanism.

SUMMARY

In a group of embodiments, an electronic device that selectively provides a recommendation is described. This electronic device may include: one or more sensors; and an integrated circuit. During operation, the integrated circuit acquires, using the one or more sensors, a measurement within an environment that is external to the electronic device, where the measurement provides information associated with a person located in a driver's position in a vehicle, and the measurement includes a non-contact measurement. Then, the integrated circuit assesses situational awareness of the person based at least in part on the measurement. Moreover, the integrated circuit receives a request associated with a partial or fully autonomous vehicle application to transition to manual control of the vehicle. In response to the request, the integrated circuit selectively provides the recommendation to the partial or fully autonomous vehicle application to transition to manual control of the vehicle based at least in part on the situational awareness.

Note that the one or more sensors may include a transmitter that transmits wireless signals and a receiver that receives wireless-return signals.

Moreover, the request may correspond to an occurrence of an unknown or an unsafe driving condition associated with operation of the vehicle.

Furthermore, the situational awareness may indicate an awareness of the person of to a current driving condition associated with operation of the vehicle.

Additionally, the situational awareness may include a physiological state and/or an inferred emotional state of the person. For example, the physiological state may include: an awake state, an alert state, and/or an oriented state. Alternatively or additionally, the physiological state may include a vital sign of the person. In some embodiments, the physiological state may include a change in the vital sign corresponding to a change in a driving condition associated with operation of the vehicle.

Note that, when the recommendation is not provided, the integrated circuit may selectively provide a second recommendation to the partial or fully autonomous vehicle application to not transition to manual control of the vehicle based at least in part on the request and the situational awareness.

Another embodiment provides a vehicle that includes the electronic device.

Another embodiment provides a computer-readable storage medium for use with the electronic device. This computer-readable storage medium may include program instructions that, when executed by the electronic device, causes the electronic device to perform at least some of the aforementioned operations of the electronic device.

Another embodiment provides a method. This method includes at least some of the operations performed by the electronic device.

This Summary is provided for purposes of illustrating some exemplary embodiments, so as to provide a basic understanding of some aspects of the subject matter described herein. Accordingly, it will be appreciated that the above-described features are examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
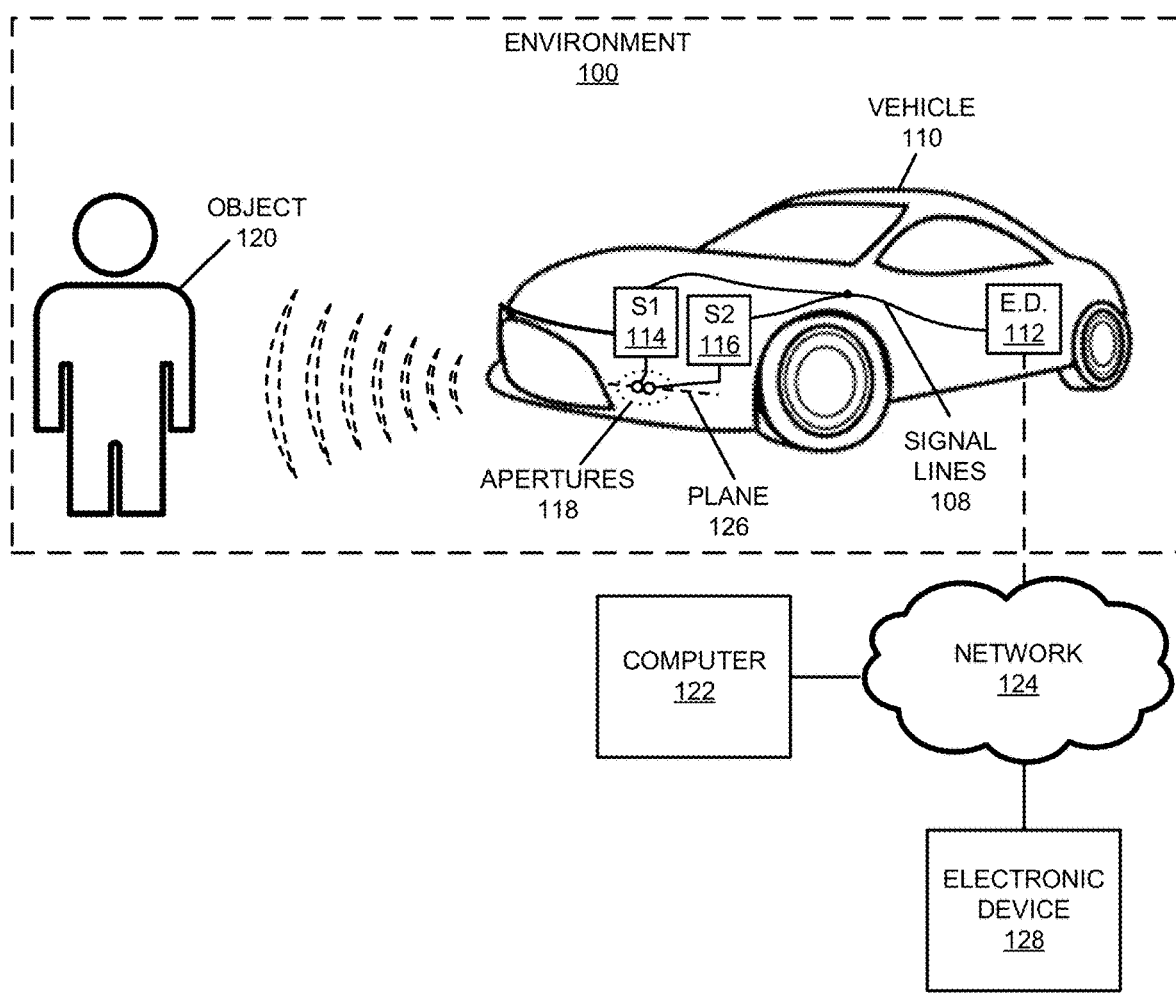
FIG. 1 is a drawing illustrating an example of an environment that includes a vehicle in accordance with an embodiment of the present disclosure.

In a group of embodiments, an electronic device that selectively provides a recommendation is described. During operation, the electronic device may acquire, using one or more sensors, a measurement within an environment that is external to the electronic device, where the measurement provides information associated with a person located in a driver's position or seat in a vehicle (who is sometimes referred to as a 'potential driver'), and the measurement includes a non-contact measurement. Then, the electronic device may assess situational awareness of the person based at least in part on the measurement. Moreover, the electronic device may receive a request associated with a partial or fully autonomous vehicle application to transition to manual control of the vehicle. In response to the request, the electronic device may selectively provide the recommendation to the partial or fully autonomous vehicle application to transition to manual control of the vehicle based at least in part on the situational awareness. Alternatively, when the recommendation is not provided, the electronic device may selectively provide a second recommendation to the partial or fully autonomous vehicle application to not transition to manual control of the vehicle based at least in part on the situational awareness.

By facilitating adaption of the transition to manual control of the vehicle based at least in part on the situational awareness of the potential driver, these feedback techniques may improve the performance of self-driving technology (such as the partial or fully autonomous vehicle application). Notably, the recommendation may only be provided when the potential driver is capable of effectively manually controlling the vehicle. For example, the situational awareness may include a physiological state and/or an inferred emotional state of the potential driver, such as a change in a vital sign corresponding to a change in a driving condition associated with operation of the vehicle. Thus, if there is a potentially dangerous situation, which is leads the partial or fully autonomous vehicle application to provide the request, and the potential driver reacts in a manner indicative of fear or alarm (but not panic, in which fear is uncontrollable and a person is often unable to think rationally or to respond in a controlled or appropriate manner to an imminent threat), they may be situationally aware and capable of assuming effective manual control. In this way, the feedback techniques may help ensure that a transition to manual control of the vehicle occurs when it is likely to be positive or constructive as a safety measure or failsafe. Consequently, the feedback techniques may help reduce an accident rate and/or improve a safety performance of self-driving technology.

In the discussion that follows, radar is used as an illustrative example of a measurement or sensor technique. For example, the radar may involve radar signals having a fundamental frequency of 1-10 GHz, 24 GHz, 77-81 GHz, 140 GHz, and/or another electromagnetic signal having a fundamental frequency in the radio or microwave frequency band. Moreover, the radar signals may be continuous wave and/or pulsed, may modulated (such as using frequency modulation or pulse modulation) and/or may be polarized (such as horizontal polarization, vertical polarization or circular polarization). Notably, the radar signals may be frequency-modulated continuous-wave, pulse-modulated continuous-wave, multiple-input multiple-output (MIMO), etc. However, a wide variety of measurement or sensor techniques may be used in conjunction with or to implement the disclosed embodiments. For example, the measurement or sensor techniques may include: optical imaging in the visible spectrum or a visible frequency band, infrared, sonar, FLIR, optical imaging having a dynamic range or contrast ratio exceeding a threshold value (such as 120 dB), lidar, an acoustic measurement (e.g., using an acoustic signal in an audible frequency band), an ultrasound measurement, etc. While many of the embodiments use one or more non-contact measurement techniques, in other embodiments one or more 'direct' (in-contact) measurement techniques may be used, such as: a vital sign measurement, an impedance measurement (such as an galvanometric measurement of skin impedance, or an AC or DC impedance measurement), etc.

Moreover, in the discussion that follows, the electronic device may communicate using one or more of a wide variety of communication protocols. For example, the communication may involve wired and/or wireless communication. Consequently, the communication protocols may include: an Institute of Electrical and Electronics Engineers (IEEE) 802.11 standard (which is sometimes referred to as 'Wi-Fi®,' from the Wi-Fi Alliance of Austin, Tex.), Bluetooth® (from the Bluetooth Special Interest Group of Kirkland, Wash.), another type of wireless interface (such as another wireless-local-area-network interface), a cellular-telephone communication protocol (e.g., a 3G/4G/5G communication protocol, such as UMTS, LTE), an IEEE 802.3 standard (which is sometimes referred to as 'Ethernet'), etc. In the discussion that follows, Ethernet and universal serial bus (USB) are used as illustrative examples.

We now describe some embodiments of the security and the feedback techniques. FIG. 1 presents a drawing illustrating an example of an environment 100 that includes a vehicle 110. For example, vehicle 110 may include: a car or automobile, a bus, a truck, etc., and more generally one that includes one or more non-retractable wheels in contact with a surface (such as a road or the ground) during operation. As described further below with reference to FIG. 2, vehicle 110 may include an electronic device (E.D.) 112 that collects or acquires one or more measurements associated with different types of sensors. Notably, while stationary (e.g., when parked), vehicle 110 may acquirement one or more measurements using a sensor (S1) 114. As discussed further below, in some embodiments vehicle 110 may optionally acquire (either with the one or more measurements or subsequently as part of a predefined preventive action) one or more additional measurements using optional sensor (S2) 116, where sensor 114 is a different type of sensor than sensor 116. Note that sensors 114 and 116 may be included in electronic device 112. Alternatively, sensors 114 and 116 may be coupled to electronic device 112, such as by electrical signal lines, optical signal lines, a cable and/or a bus, which is illustrated by signal lines 108.

Moreover, in order to obtain accurate and useful sensor information about environment 100, sensors 114 and 116 may be in the same plane or may be coplanar in plane 126. In addition, apertures 118 of or associated with sensors 114 and 116 may be adjacent to each other or may be co-located (i.e., at the same location on vehicle 110). This may ensure that sensors 114 and 116 capture or obtain sensor information of substantially the same portions of environment 100 and objects (such as object 120) in environment 100. Therefore, sensors 114 and 116 may have at least substantially overlapping fields of view in environment 100, such as fields of view that are more than 50, 75, 80 or 90% in common.

In some embodiments, sensor 114 performs radar measurements of radar information, and sensor 116 performs optical imaging in a visible spectrum or a visible frequency band (such as at least a frequency between 430 and 770 THz or at least a wavelength between 390 and 700 nm). However, more generally, sensors 114 and 116 may perform at least a pair of different measurements. For example, sensors 114 and 116 may include two or more of: a radar sensor, an optical imaging sensor in the visible spectrum or the visible frequency band, an infrared sensor, a FLIR sensor, a sonar sensor, an optical imaging sensor having a dynamic range or contrast ratio exceeding a threshold value (such as 120 dB), lidar, etc. More generally, as described further below with reference to FIGS. 3-6, sensor 114 may acquire one or more measurements of object 120 (such as a person) that, using one or more estimation techniques (such as a pre-trained or a dynamically adapted/self-learning predictive model, e.g., a machine-learning classifier or regression model, and/or a neural network), may be estimated to have an intent. When the estimated intent is associated with a type of adverse event (such as theft, property damage, and/or another type of crime), electronic device 112 and/or vehicle 110 may perform a preventive action, prior to an occurrence of the type of adverse event, in order to prevent the occurrence of the type of event, reduce a probability of the occurrence of the type of adverse event, or reduce an amount of financial damage associated with the occurrence of the type of adverse event. Note that a given sensor may be capable of transmitting and/or receiving signals.

Figure 2:
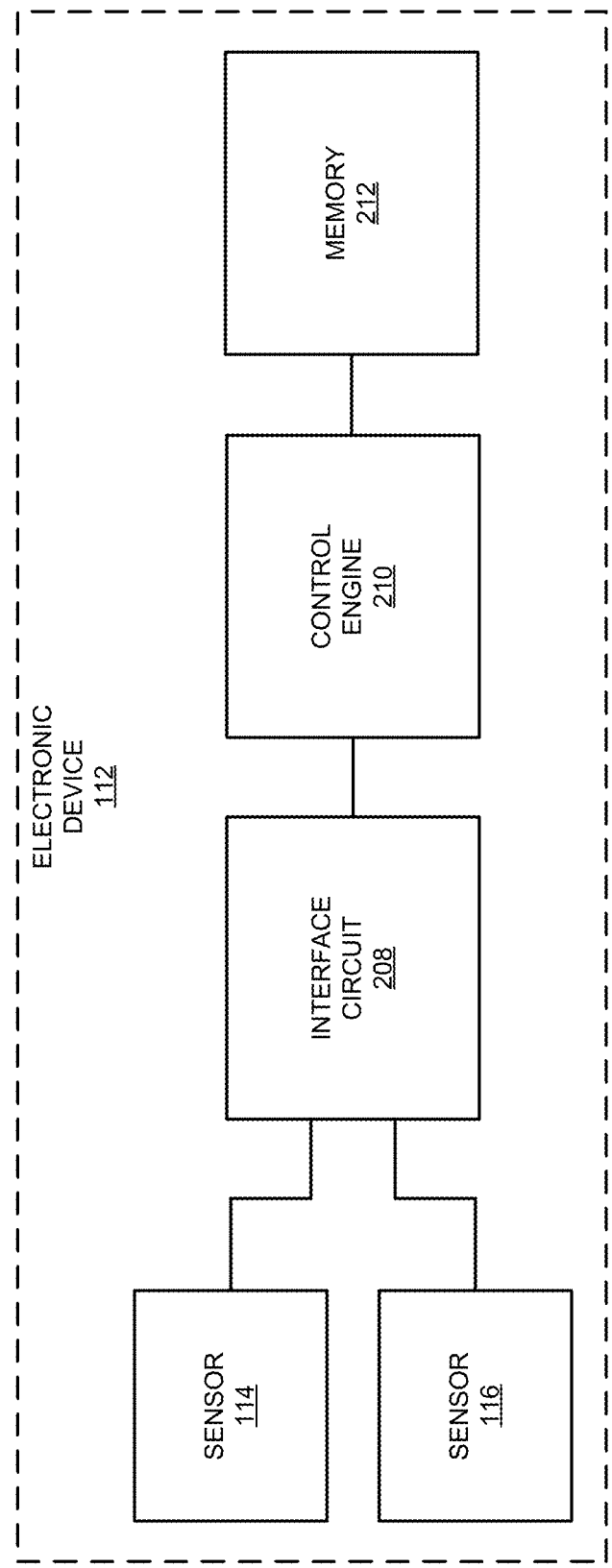
FIG. 2 is a block diagram illustrating an example of an electronic device that can included on the vehicle in FIG. 1 in accordance with an embodiment of the present disclosure.

FIG. 2 presents a block diagram illustrating an example of electronic device 112. As described further below with reference to FIG. 15, this electronic device may include a control engine 210 (such as an integrated circuit and/or a processor, which are sometimes referred to as 'control logic') that performs at least some of the operations in the security or feedback techniques. Notably, control engine 210 may provide, via interface circuit 208, one or more signals or instructions to sensor 114 and optional sensor 116 (which may be included in or coupled to electronic device 112, and thus are optional in electronic device 112 in FIG. 2) to acquire, respectively, one or more measurements in an environment that includes electronic device 112. For example, sensor 114 may measure radar information, and sensor 116 may measure an optical image. Then, sensor 114 and/or sensor 116 may provide the one or more measurements to control engine 210. In some embodiments, the one or more measurements include one or more associated timestamps when the one or more measurements were acquired. Alternatively, control engine 210 may generate the one or more timestamps when the one or more measurements are received.

Next, control engine 210 may store the one or more measurements (or information that specifies one or more results of the one or more measurements) in memory 212. For example, as described further below with reference to FIG. 3, the one or more measurements may be stored in associated memory locations. In some embodiments, the one or more measurements are stored in memory along with the one or more timestamps and/or location information that specifies where the one or more measurements were acquired (such as GPS information, location information associated with a local positioning system, e.g., from a WLAN, location information associated with a cellular-telephone network, etc.).

Furthermore, control engine 210 may optionally perform one or more quality-control operations on the one or more measurements. For example, control engine 210 may analyze a light intensity or luminance level in an optical image and may compare the luminance level to a threshold value. Alternatively or additionally, control engine 210 may analyze the optical image or the radar information to determine a signal-to-noise ratio, and then may compare the signal-to-noise ratio to another threshold value. In some embodiments, control engine 210 may analyze the one or more measurements to confirm that each include information associated with the same object (such as object 120 in FIG. 1).

Based on the results of the one or more quality-control operations, control engine 210 may perform a remedial action. For example, control engine 210 may store a quality-control metric with the one or more measurements in memory 212, such as a quality-control metric that indicates 'pass' (such as when the luminance level exceeds the threshold value, the signal-to-noise ratio exceeds the other threshold value and/or that the one or more measurements include information associated with the same object), 'fail' (such as when the luminance level is less than the threshold value, the signal-to-noise ratio is less than the other threshold value and/or the one or more measurements do not include information associated with the same object) or 'further analysis required' (such as when the results of the one or more quality-control operations are mixed). Alternatively, control engine 210 may erase the one or more measurements when either fails the one or more quality-control operations.

Separately or additionally, in some embodiments quality control is optionally performed while the one or more measurements are acquired. For example, when performing a measurement using sensor 114 and/or a measurement using sensor 116, control engine 210 (and/or sensor 114 or sensor 116, respectively) may determine an environmental condition (such as light intensity, e.g., a luminance level, a weather condition such as fog, a temperature, e.g., greater than 90 F, etc.) and/or information associated with an object (such as object 120 in FIG. 1). For example, control engine 210 may determine whether the object is two dimensional (such as a sign) or three dimensional (such as a person or an animal). Then, based on the determined environmental condition and/or information associated with the object, control engine 210 (and/or sensor 114 or sensor 116, respectively) may perform a remedial action. For example, control engine 210 may increase a transmit power of radar signals, or may use different filtering and/or a longer integration time in conjunction with an infrared sensor. Alternatively or additionally, control engine 210 may provide one or more signals or instructions to a light source in or coupled to electronic device 112 (such as a light source included in or associated with sensor 114 and/or 116) so that selective illumination is output, such as a two or three-dimensional array of dots, a pattern of stripes, an illumination pattern, etc. This selective illumination may improve the ability to resolve structure of a three-dimensional object. In some embodiments, control engine 210 may provide one or more signals or instructions to a light source in or coupled to electronic device 112 (such as a light source, e.g., a vertical-cavity surface-emitting laser or vcsel, included in or associated with sensor 114 and/or 116) so that illumination having a wavelength is output (e.g., illumination at a particular wavelength). This constant-wavelength illumination may allow the one or more measurements to be acquired when the signal-to-noise ratio is low.

Note that electronic device 112 may be positioned on or proximate to a surface of vehicle 110 in FIG. 1 (such as a front, back or side surface). Alternatively, electronic device 112 may be mounted or positioned on a top surface (such as a roof) of vehicle 110 and an aperture of electronic device 112 may rotate about a vertical axis, so that it 'sweeps' an arc (e.g., 120°, 180° or 360°).

In some embodiments, electronic device 112 (FIGS. 1 and 2) and/or vehicle 110 includes fewer or additional components, two or more components are combined into a single component and/or positions of one or more components are changed.

Figure 3:
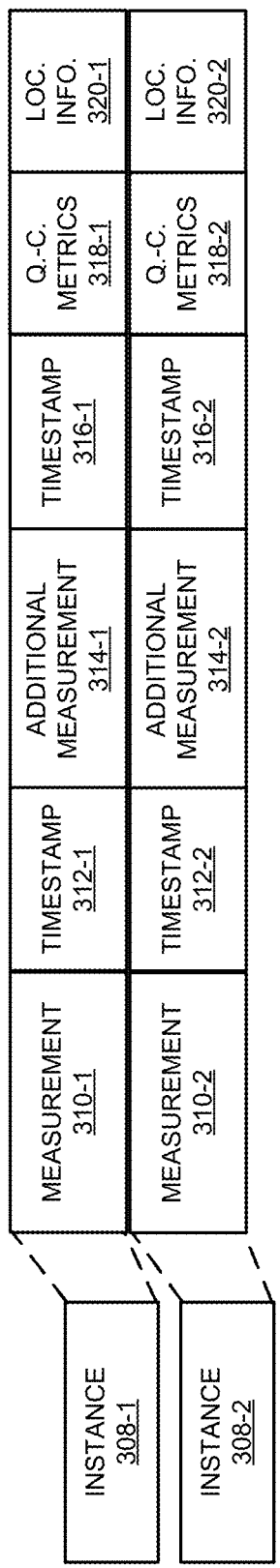
FIG. 3 is a block diagram illustrating an example of a data structure for use in conjunction with, e.g., the electronic device of FIGS. 1 and 2 in accordance with an embodiment of the present disclosure.

FIG. 3 presents a block diagram illustrating an example of a data structure 300 for use in conjunction with electronic device 112 (FIGS. 1 and 2), such as in memory in or associated with electronic device 112 (FIGS. 1 and 2). Notably, data structure 300 may include: one or more instances 308 of measurement 310, optional associated timestamps 312 for measurements 310, one or more instances of additional measurements 314, optional associated timestamps 316 for additional measurements 314, one or more quality-control (Q.-C.) metrics 318 associated with the one or more instances of measurements 310 and/or associated with the one or more instances of measurements 314, and/or location information 320 where the one or more instances of measurements 310 and/or 314 were acquired. Note that data structure 300 may include fewer or additional fields, two or more fields may be combined, and/or a position of a given field may be changed. For example, data structure may include information extracted from measurements 310 and/or additional measurements 314. In some embodiments, where measurements 310 include radar measurements, the extracted information may include a range to the object, an angle of arrival of the radar measurements and/or a velocity of the object (such as based at least in part on Doppler measurements).

Figure 4:
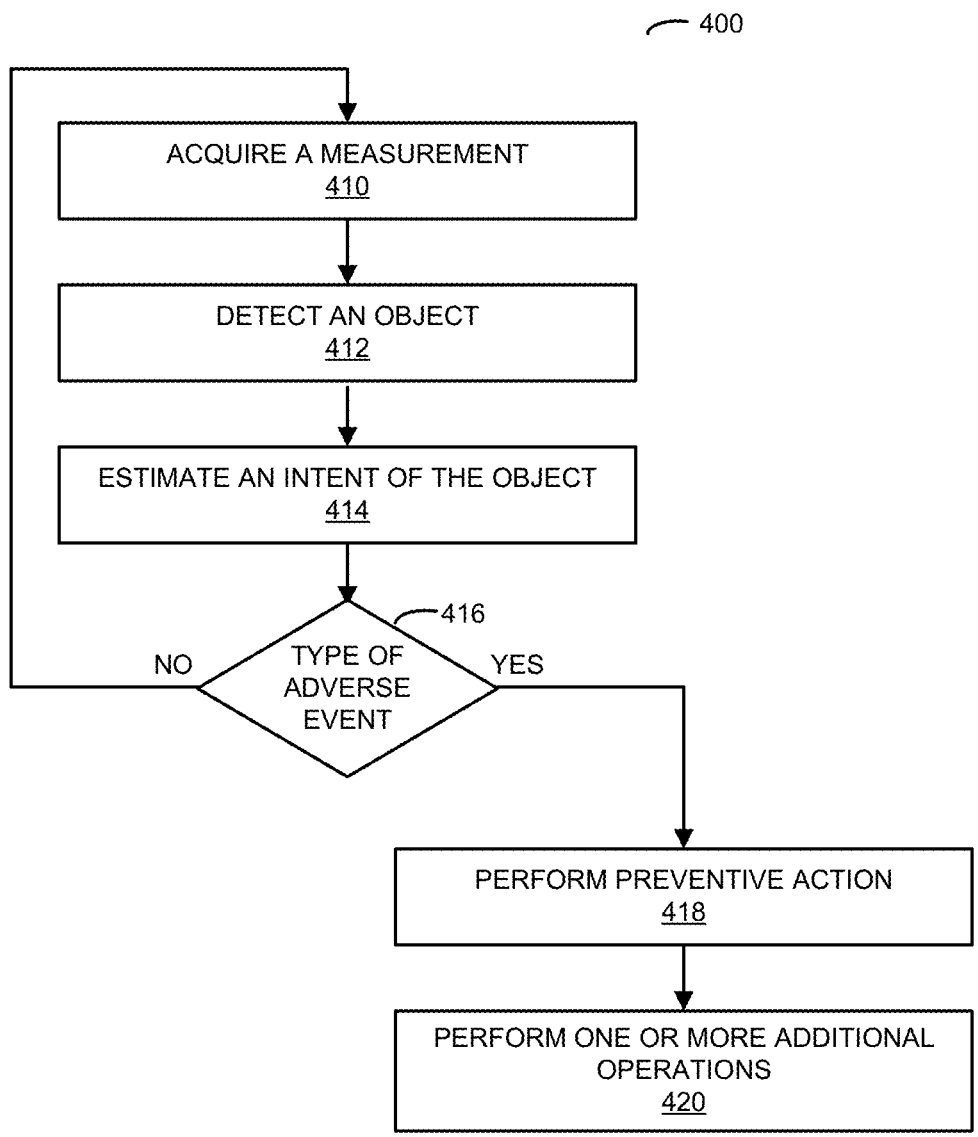
FIG. 4 is a flow diagram illustrating an example of a method for selectively performing a preventive action in accordance with an embodiment of the present disclosure.

FIG. 4 presents a flow diagram illustrating an example of a method 400 for selectively performing a preventive action. This method may be performed by an electronic device (such as electronic device 112 in FIGS. 1 and 2) or a component in the electronic device (such as an integrated circuit or a processor). During operation, the electronic device may acquire, using one or more sensors, a measurement (operation 410) in an environment that is external to the electronic device, where the measurement provides information associated with an object, and the measurement is a non-contact measurement. For example, the one or more sensors may include a transmitter that transmits wireless signals and a receiver that receives wireless-return signals. In some embodiments, the one or more sensors include two or more different types of sensors (such as a radar sensor and an optical sensor), and the measurement is acquired using the two or more different types of sensors.

Then, the electronic device may detect the object (operation 412) based at least in part on the measurement. For example, the electronic device may apply one or more pretrained neural networks (e.g., a convolutional neural network) to the measurement to detect and/or to identify/classify the object. The one or more neural networks may be arranged in or may define a classification hierarchy to iteratively detect and/or identify the object, such as animal/non-animal, then human/non-human animal, etc., vehicle/non-vehicle, type of vehicle, etc., or street sign/non-street sign, type of street sign, etc. Alternatively or additionally, a wide variety of analysis and/or identification techniques may be used to extract features from the measurement (e.g., an image), such as one or more of: normalizing a magnification or a size of the object, rotating the object to a predefined orientation, extracting the features that may be used to detect and/or identify the object, etc. Note that the extracted features may include: edges associated with one or more potential objects, corners associated with the potential objects, lines associated with the potential objects, conic shapes associated with the potential objects, color regions in the measurement, and/or texture associated with the potential objects. In some embodiments, the features are extracted using a description technique, such as: scale invariant feature transform (SIFT), speed-up robust features (SURF), a binary descriptor (such as ORB), binary robust invariant scalable keypoints (BRISK), fast retinal keypoint (FREAK), etc. Furthermore, the electronic device may apply one or more supervised or machine-learning techniques to the extracted features to detect and/or identify/classify the object, such as: support vector machines, classification and regression trees, logistic regression, LASSO, linear regression and/or another (linear or nonlinear) supervised-learning technique.

Moreover, the electronic device may extract a signature associated with the object from the measurement (e.g., radar information). Extracting the signature may involve at least some of the processing of reflected radar signals to extract radar information. For example, the electronic device may perform windowing or filtering, one or more Fourier or discrete Fourier transforms (with at least 128 or 256 bits), peak detection, etc. In some embodiments, a constant false alarm rate (CFAR) technique is used to detect and/or determine whether a peak in the radar information is significant. Notably, the electronic device may calculate statistical metrics (such as a mean and a standard deviation) for a given range, and the electronic device may determine if a given peak is significant based on the calculated statistical metrics at different ranges. This approach may allow the electronic device, separately or in conjunction with processing by a remotely located electronic device (such as a cloud-based computer), to statistically detect and/or identify the radar information of the object.

The resulting signature of the object may include multiple dimensions. For example, the signature may include one or more of: a range to the object, a first angle to the object along a first axis (such as a horizontal axis), Doppler information associated with the object and/or a second angle to the object along a second axis (such as a vertical axis).

Moreover, the electronic device may estimate an intent of the object (operation 414) based at least in part on the measurement (and/or information extracted from the measurement or that is determined based at least in part on analysis of the measurement). For example, the object may include or may be a person, the electronic device may identify the person (such as by comparing the measurement to a predetermined dataset of measurements and associated individual identities), and the intent may be estimated based at least in part on the identity of the person. Notably, if the person is known and is considered 'friendly' (such as a registered owner of the electronic device, or a person that has been previously identified one or more times and who is consequently considered low risk or harmless), the estimated intent may be 'neural' or 'positive' (and, thus, a risk for a type of adverse event, such as theft, property damage, and/or another type of crime, may be low). Alternatively, the object may include or may be a person having an unknown identity, and the intent may be estimated based at least in part on an association of the person with one or more prior occurrences of the type of adverse event in an event history. For example, while the person may be unknown, there may be one or more repeated occurrences of the type of adverse event when the unknown person was in proximity (such as reported or captured occurrences that are stored, locally or remotely, in an event history). Consequently, in this example, the unknown person may be deemed 'unfriendly', so the corresponding estimated intent may be 'negative' (and, thus, a risk for the type of adverse event may be high).

Note that in embodiments where the object may include or may be a person, the intent may be estimated based at least in part on: an inferred emotional state of the person (such as a facial expression, a posture, a tone of voice, etc., that indicates that the person is angry or hostile); a behavior of the person (such as when the person appears intoxicated or under the influence of a drug, when the person appears violent, when the person is acting secretive or in a surreptitious manner, e.g., the person is acting like they are doing something wrong or that they have something to hide, when the person's face is at least partially hidden or obscured, etc.); and/or a vital sign of the person (such as a pulse rate or a respiration rate), which is specified by the measurement (such as a radar measurement). For example, an emotional state may be estimated or inferred by using one or more measurements (such as the one or more measurements) as inputs to a pretrained neural network or a machine-learning model that outputs an estimate of an emotional state (such as a probability of a particular emotional state or a classification in a particular emotional state). In some embodiments, the measurement may provide information associated with a second object that is related to the object, the electronic device may identify the second object (such as a tool carried by the person, e.g., a crowbar, spray paint or a brick, which may be identified by comparing the measurement to a predetermined annotated dataset of measurements and associated classifications), and the intent may be estimated based at least in part on the identified second object.

Next, when the estimated intent is associated with the type of adverse event (operation 416), the electronic device may perform the preventive action (operation 418) prior to an occurrence of the type of adverse event, where the preventive action reduces a probability of the occurrence of the type of adverse event or an amount of financial damage associated with the occurrence of the type of adverse event. Otherwise (operation 416), the electronic device may repeat method 400, e.g., at operation 410.

For example, the measurement may be acquired using a first sensor in the one or more sensors, and the preventive action may include acquiring, using a second sensor in the one or more sensors, a second measurement that provides information associated with the object. Notably, the measurement may include a radar measurement, and the second measurement may include an image (such as a picture or a video), which may be stored in memory 212 (FIG. 2), in remotely located memory (such as in cloud-based storage), presented on a display in a vehicle, and/or provided to a remotely located electronic device or computer (such as another electronic device of or associated with: an owner of the electronic device or the vehicle, a security service, and/or law enforcement). More generally, the preventive action may include providing information about the object to a law enforcement agency and/or contacting a law enforcement agency (e.g., an indicating that a type of adverse event may be occurring or may be about to occur).

In some embodiments, the electronic device may include a light source, and the preventive action may include selectively illuminating the object using the light source. Alternatively or additionally, the electronic device may include an alarm, and the preventive action may include selectively activating the alarm. Furthermore, the electronic device may include a display, and the preventive action may include selectively presenting information about the object on the display (e.g., as noted previously, the measurement, such as an image of the object, may be presented on the display).

Moreover, the electronic device may include a lock, and the preventive action may include: determining a state of the lock; providing an electronic signal that sets the lock into a locked state when the lock is initially in an unlocked stated; and disabling an ability to change the state of the lock. Alternatively or additionally, the electronic device may include a vehicle, and the preventive action may include disabling movement of the vehicle.

In some embodiments, the electronic device may perform one or more optional additional operations (operation 420). For example, the electronic device may include a battery, and the electronic device may perform at least one of the acquiring (operation 410), the detecting (operation 412), the estimating (operation 414) and the performing (operation 418) using a dynamic subset of resources in the electronic device based at least in part on: a discharge current of the battery and/or a remaining charge of the battery.

Note that the electronic device may be a portable or removable electronic device, such as a measurement or sensor module that is installed in or integrated into the vehicle.

In embodiments in which the one or more measurements include radar measurements, the electronic device may measure radar information using a variety of antenna configurations. For example, the electronic device 112 (or sensor 114 in FIGS. 1 and 2) may include multiple antennas. Different subsets of these antennas may be used to transmit and/or receive radar signals. In some embodiments, a first subset of the antennas used to transmit radar signals and a second subset of the antennas used to receive reflected radar signals may be dynamically adapted, such as based on environmental conditions, a size of the object, a distance or range to the object, a location of the object relative to a vehicle, etc. By varying the number of transmit and receive antennas, the angular resolution of the radar can be changed. Notably, one transmit antenna and four receive antennas (1T/4R) may have an angular resolution of approximately 28.5°, two transmit antennas and four receive antennas (2T/4R) may have an angular resolution of approximately 15°, three transmit antennas and four receive antennas (3T/4R) may have an angular resolution of approximately 10°, etc. More generally, the angular resolution with one transmit antenna and N receive antennas (1T/NR), where N is a non-zero integer, may be approximately 114°/N. Thus, if there is one transmit antenna and 192 receive antennas, the angular resolution may be less than one degree. For automotive applications, an angular resolution may be a few degrees at a distance of 200-250 m. As described further below with reference to FIG. 15, note that the transmit and/or receive antennas may be physical antennas or may be virtual antennas in an adaptive array, such as a phased array.

Moreover, in some embodiments, the transmit antenna(s) has 6-30 dB gain, a beam width between a few degrees and 180°, a transmit power of up to 12 dBm, and an effective range of up to 200-250 m. Furthermore, there may be one transmit antenna and one receive antenna (1T/1R), three transmit antennas and four receive antennas (1T/4R), three transmit antenna and four receive antennas (3T/4R), MIMO for spatial diversity, etc. Furthermore, the location(s) or positions of the transmit and/or the receive antenna(s) may be selected to increase a horizontal and/or a vertical sensitivity. For example, an antenna may be displaced relative to another antenna along a vertical or a horizontal axis or direction by one half of a fundamental or carrier wavelength of the radar signals to increase the (respectively) vertical or horizontal sensitivity.

Figure 5:
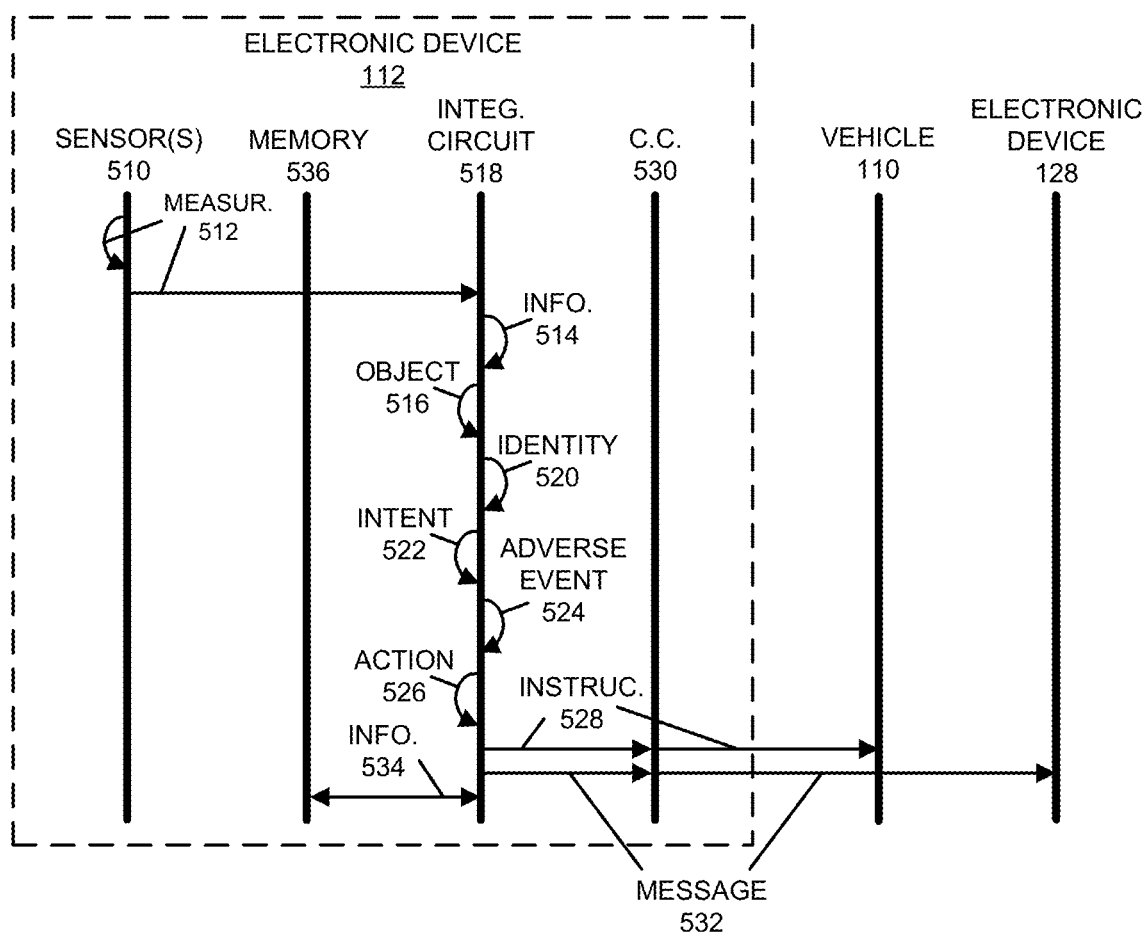
FIG. 5 is a drawing illustrating an example of communication among components, e.g., in the electronic device of FIGS. 1 and 2 in accordance with an embodiment of the present disclosure.

Embodiments of the security techniques are further illustrated in FIG. 5, which presents a drawing illustrating an example of communication among components in electronic device 112, vehicle 110 and electronic device 128. Notably, sensor(s) 510 in electronic device 112 may acquire one or more measurements 512 in an environment that is external to electronic device 112, where the one or more measurements 512 provide information 514 associated with an object 516, and the one or more measurements 512 include a non-contact measurement. Then, an integrated circuit (I.C.) 518 in electronic device 112 may detect object 516 based at least in part on the one or more measurements 512. For example, integrated circuit 518 may analyze the one or more measurements 512 to determine information 514, which is then used to detect object 516. In some embodiments, integrated circuit 518 may optionally identify 520 object 516.

Moreover, integrated circuit 518 may estimate an intent 522 of object 516 based at least in part on the one or more measurements 512, information 514, and/or identification 520. When the estimated intent 522 is associated with a type of adverse event 524, integrated circuit 518 may perform a preventive action 526 prior to an occurrence of the type of adverse event 524.

For example, integrated circuit 518 may provide instruction 528 to communication circuit (C.C.) 530 in electronic device 112, which provides instruction 528 to vehicle 110 (e.g., in one or more packets or frames). In response to instruction 528, vehicle 110 may: turn on a light source, activate an alarm, change a state of a lock, disable movement of vehicle 110, present information about object 516 on a display in vehicle 110 (such as the one or more measurements 512, information 514 and/or identity 520), etc. Alternatively or additionally, integrated circuit 518 may provide instruction 528 to communication circuit 530, which then provides a message 532 to electronic device 128 (which may be owned by or associated with an owner or user of electronic device 112, a security service, or a law enforcement agency). This message may include information about object 516, such as the one or more measurements 512, information 514, identity 520, and/or type of adverse event 524. Note that this information may be aggregated into an event history, which may be subsequently accessed by vehicle 110 and/or another vehicle in order to assist in estimating intent 522 during one or more future events. Alternatively or additionally, information 534 corresponding to the event history may be stored in memory 536 in electronic device 112.

While the preceding discussion illustrated electronic device 112 locally performing operations in the security techniques (e.g., in real-time), in other embodiments at least some of the operations may be, at least in part, performed by another electronic device (such as vehicle 110, i.e., in proximity to electronic device 112, and/or a remotely located electronic device, such as a cloud-based computer 122 in FIG. 1). For example, electronic device 112 may pre-process the one or more measurements 512, and detection of object 516, determining of identity 520 and/or estimating intent 522 may be performed, at least in part, by a cloud-based computer 122 (FIG. 1) that is accessed via communication using network 124 in FIG. 1 (such as via wireless communication in a WLAN or a cellular-telephone network and/or via wireless communication, e.g., using the Internet).

Figure 6:
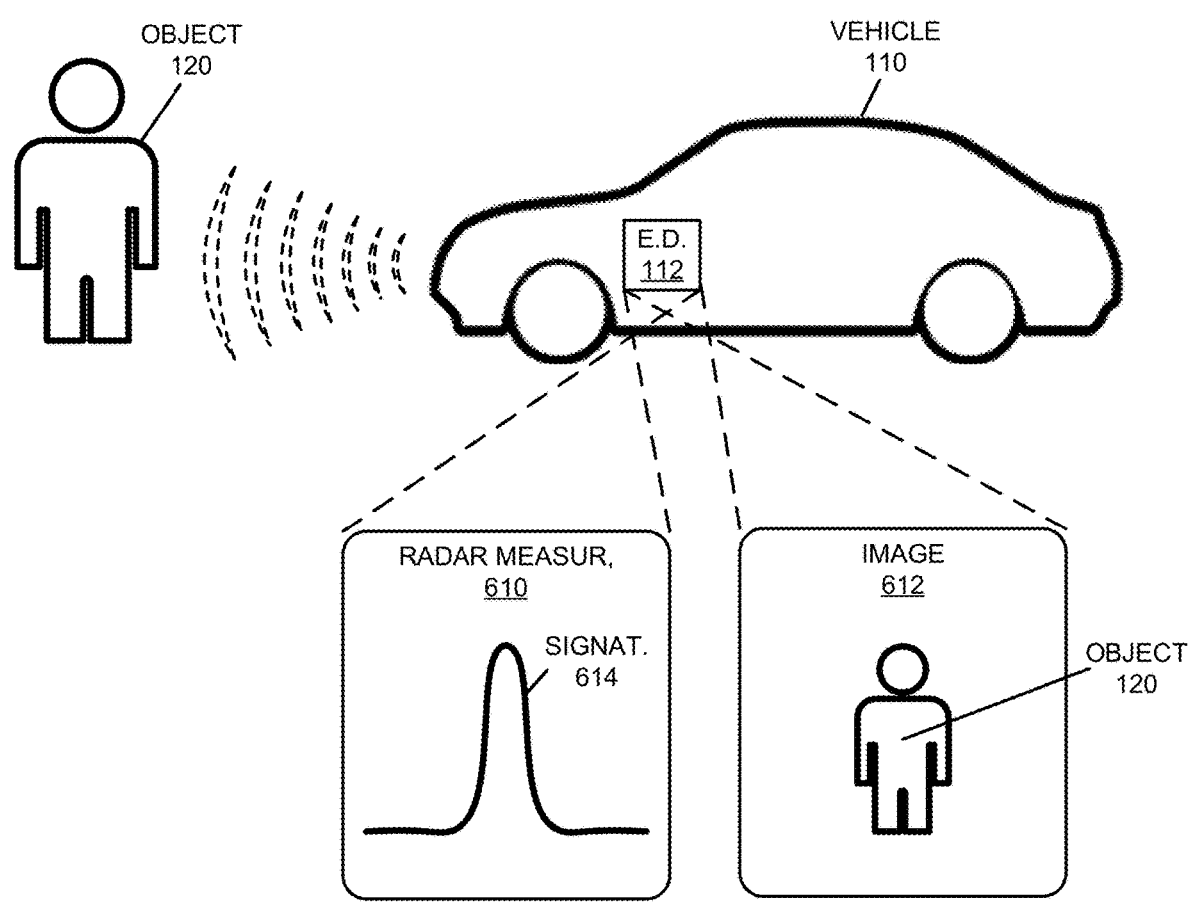
FIG. 6 is a drawing illustrating an example of selective performing of a preventive action using, e.g., the electronic device of FIGS. 1 and 2 in accordance with an embodiment of the present disclosure.

FIG. 6 presents a drawing illustrating an example of selective performing of a preventive action using electronic device 112 (FIGS. 1 and 2). Notably, sensor(s) in electronic device 112 may, continuously, periodically or as needed, acquire one or more measurements in an environment that is external to electronic device 112, where the one or more measurements provide information associated with object 120, and the one or more measurements include a non-contact measurement. For example, the one or more measurements may include radar measurements 610 and an optical measurement (such as capturing an image 612). Then, electronic device 112 may analyze the radar measurements 610 to detect object 120, including extracting a signature 614 associated with object 120 and/or to determine one or more vital signs (such as a pulse and/or a respiration rate). Moreover, electronic device 112 may analyze image 612 to detect object 120. In some embodiments, electronic device 112 may use information in image 612 to identify object 120 (such as inputs to a pretrained neural network or a machine-learning model). This may include classifying object 120 and/or identifying a particular person (such as by using face or biometric recognition). In general, the information provided by the one or more measurements may be compared or jointly analyzed in order to detect and/or to identify object 120.

Next, electronic device 112 may estimate an intent of object 120. For example, based at least in part on signature 614 and/or the identity of object 120, electronic device 112 may determine whether object 120 (such as a particular person) is known and considered friendly or safe, or not. This may involve a comparison with historical records of previous measurements on objects and subsequent events (such as the occurrence or the absence of an occurrence of a type of adverse event) by electronic device 112 and/or one or more other instances of electronic device 112 (which may be shared or may be stored in in memory in a remotely accessible cloud-based computer), predefined relationships with electronic device 112 (such as a specified owner of electronic device 112 or a trusted person), an inferred relationship (such as an individual who has been previously observed to be in proximity to the specified owner of electronic device 112 or a trusted person), etc. Note that the historical records of previous measurements on objects and subsequent events may be used even if the identity of a person is unknown. For example, if an unknown person was involved in car theft in the area, electronic device 112 may compare signature 614 and the image with the records to confirm that it is the same unknown person, and then may use the prior association with a type of event to 'post-did' (using prior behavior, instead of predict) that this unknown person's estimate intent is negative or that there is a high risk for the type of adverse event. Alternatively or additionally, electronic device 112 may access police reports and/or publicly available criminal records to estimate the intent of a person.

Note that the intent may be estimated based at least in part on an inferred emotional state of the person and/or a behavior of the person. For example, the one or more measurements may indicate that a person is angry and/or drunk. In these circumstances, electronic device 112 may estimate the intent of the person as negative or hostile, and thus that there is a high risk for a type of adverse event. Alternatively or additionally, if the person is carrying a second object (such as a crowbar, burglary tools, a weapon, or spray paint), electronic device 112 may estimate the intent of the person as negative or hostile, and thus, once again, that there is a high risk for a type of adverse event. For example, the radar measurements may detect and/or identify (such as classify) the second object, even when it is under a person's clothing or in a backpack. In some embodiments, the intent is estimated based on the vital sign. For example, an elevated vital sign may indicate fear or suspicious activity. In conjunction with the image, electronic device 112 may estimate the emotional state of a person.

As discussed previously, when the estimated intent is associated with a type of adverse event (or an increased risk for the type of adverse event), electronic device 112 may perform a preventive action prior to an occurrence of the type of adverse event.

Figure 7:
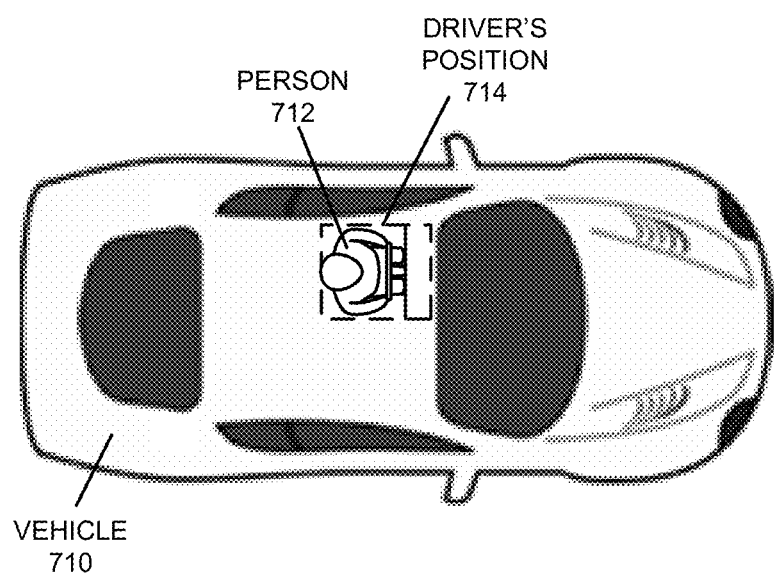
FIG. 7 is a drawing illustrating an example of an environment within a vehicle in accordance with an embodiment of the present disclosure.

While FIGS. 2-6 illustrated the use of electronic device 112 to provide enhanced security by monitoring potential threats in an external environment (such as outside of a vehicle), in other embodiments electronic device 112 may be used within a vehicle to improve self-driving technology. FIG. 7 presents a drawing illustrating an example of an environment within a vehicle 710. In this environment, a person 712 may be sitting in a driver's seat or a driver's position 714 in vehicle 710. As discussed further below, in principle, even when a partial or fully autonomous vehicle application is operating vehicle 710, person 712 may need to take over operation of vehicle 710 on short notice. However, if person 712 is distracted or unaware about what is currently happening around vehicle 710 (and what is potentially about to happen), transferring control to person 712 may be ill-advised, because an accident may still occur or an even worse outcome may result. The challenge, in this regard, is to be able to determine when person 712 is properly prepared to assume control. This is different that simply detecting whether person 712 has their hands on a steering wheel or has their foot on an accelerator or a break petal. Embodiments of the feedback techniques may be used to address this problem.

Figure 8:
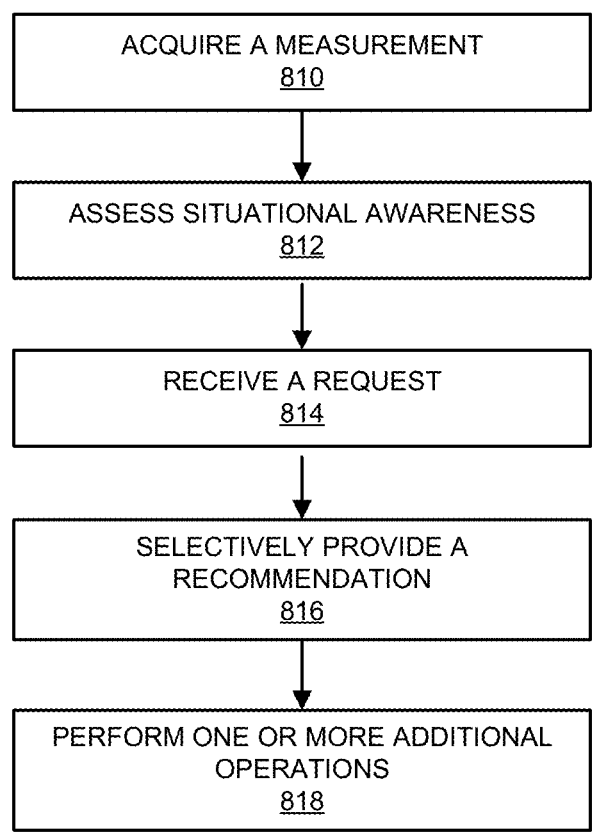
FIG. 8 is a flow diagram illustrating an example of a method for selectively providing a recommendation in accordance with an embodiment of the present disclosure.

This is shown in FIG. 8, which presents a flow diagram illustrating an example of a method 800 for selectively providing a recommendation. This method may be performed by an electronic device (such as electronic device 112 in FIGS. 1 and 2) or a component in the electronic device (such as an integrated circuit or a processor). During operation, the electronic device may acquire, using one or more sensors, a measurement (operation 810) within an environment that is external to the electronic device, where the measurement provides information associated with a person located in a driver's position in a vehicle, and the measurement includes a non-contact measurement. For example, the one or more sensors may include a transmitter that transmits wireless signals and a receiver that receives wireless-return signals. Alternatively or additionally, the one or more sensors may include an image sensor that performs optical measurements (such as capturing one or more images or a video).

Then, the electronic device may assess situational awareness (operation 812) of the person based at least in part on the measurement. Note that 'situational awareness' may include perception of environmental elements and events with respect to time or space, the comprehension of their meaning, and/or the projection of their future status. When the person or potential driver has appropriate or sufficient situational awareness, they may be better able to safely and effectively assume control of the vehicle when needed. Thus, the situational awareness may indicate an awareness of the person of to a current driving condition associated with operation of the vehicle.

In some embodiments, the situational awareness may include a physiological state and/or an inferred emotional state of the person. For example, an emotional state may be estimated or inferred by using one or more measurements (such as the one or more measurements) as inputs to a pretrained neural network or a machine-learning model that outputs an estimate of an emotional state (such as a probability of a particular emotional state or a classification in a particular emotional state).

Moreover, the physiological state may include: an awake state, an alert state, and/or an oriented state. Alternatively or additionally, the physiological state may include a vital sign of the person. Note that the physiological state may include a change in the vital sign corresponding to a change in a driving condition associated with operation of the vehicle.

Furthermore, the electronic device may receive a request (operation 814) or a message associated with a partial or fully autonomous vehicle application to transition to manual control of the vehicle. For example, the request may correspond to an occurrence of an unknown or an unsafe driving condition associated with operation of the vehicle, which may lead the partial or fully autonomous vehicle application to want to transfer control to the person.

In response to the request, the electronic device may selectively provide the recommendation (operation 816) to the partial or fully autonomous vehicle application to transition to manual control of the vehicle based at least in part on the situational awareness.

While the preceding example illustrated bilateral communication between the vehicle and the electronic device, in order to facilitate a faster or real-time response when deciding whether to transition control to the person, in some embodiments the electronic device may continuously, periodically (such as after a time interval) or as needed (such as when there is a change in the assessed situational awareness) update the vehicle as to a current assessment of the situational awareness of the person. For example, the electronic device may update information stored in memory or in a register (such as a numerical value corresponding to the assessed situational awareness or a bit indicating whether or not the person is sufficiently situationally aware). In these embodiments, the vehicle may access this stored information and, thus, may use the information when deciding whether or not to transition to manual control. Therefore, in some embodiments, instead of operations 814 and 816, the electronic device may provide information that specifies or indicates the assessed situational awareness to the vehicle or may store this information in memory, which can be accessed by the vehicle, as needed.

In some embodiments, the electronic device may perform one or more optional additional operations (operation 818). For example, when the recommendation is not provided, the electronic device may selectively provide a second recommendation to the partial or fully autonomous vehicle application to not transition to manual control of the vehicle based at least in part on the request and the situational awareness.

Note that the electronic device may be a portable or removable electronic device, such as a measurement or sensor module that is installed in or integrated into the vehicle.

Figure 9:
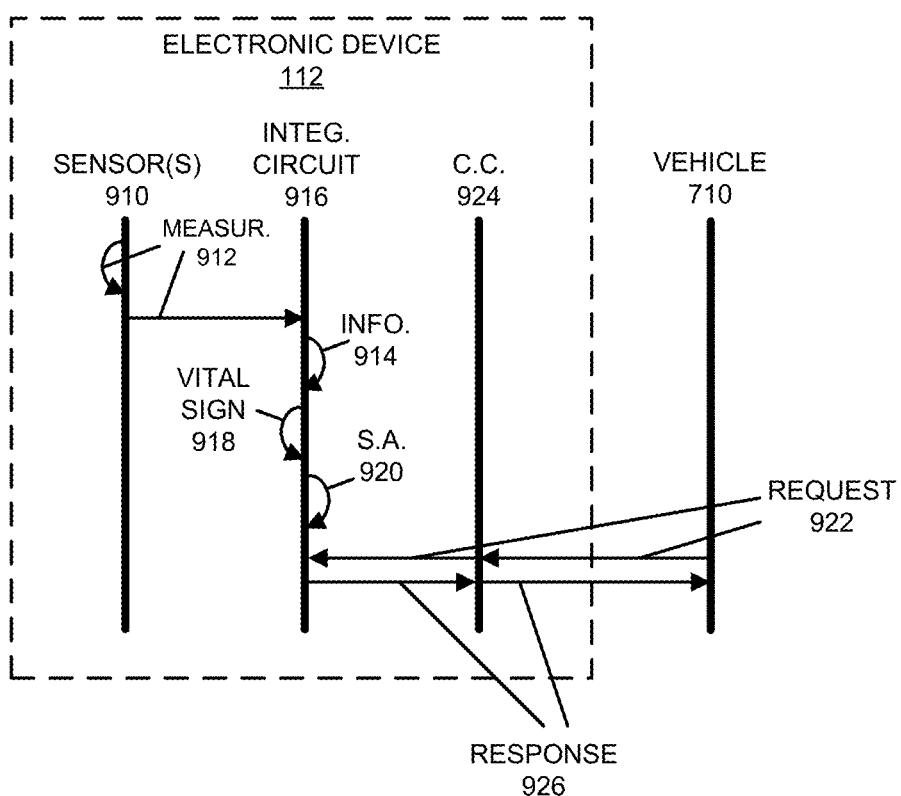
FIG. 9 is a drawing illustrating an example of communication among components, e.g., in the electronic device of FIGS. 1 and 2 in accordance with an embodiment of the present disclosure.

FIG. 9 presents a drawing illustrating an example of communication among components in electronic device 112 and vehicle 710. Notably, sensor(s) 910 in electronic device 112 may acquire one or more measurements 912 in an environment that is external to electronic device 112, where the one or more measurements 912 provide information 914 associated with a person located in a driver's position in vehicle 710, and the one or more measurements 912 include a non-contact measurement.

Then, an integrated circuit (I.C.) 916 in electronic device 112 may extract information 914 from the one or more measurements 912, and may assess situational awareness (S.A.) 920 of the person based at least in part on the one or more measurements 912 and/or information 914. For example, situational awareness 920 may include a physiological state and/or an inferred emotional state of the person. Notably, the physiological state may include a change in the vital sign corresponding to a change in a driving condition associated with operation of vehicle 710. Thus, in some embodiments, integrated circuit 916 may determine a vital sign 918 of the person based at least in part on the one or more measurements 912.

Moreover, in response to an occurrence of an unknown or an unsafe driving condition associated with operation of vehicle 710, a partial or fully autonomous vehicle application executed in an environment of vehicle 710 (such as in an operating system environment) may provide a request 922 to electronic device 112 to transition to manual control of vehicle 710 (i.e., to have the person drive vehicle 710). After receiving request 922, a communication circuit 924 in electronic device 112 may provide request 922 to integrated circuit 916. Then, in response to request 922, integrated circuit 916 may, via communication circuit 924, selectively provide recommendation 926 to the partial or fully autonomous vehicle application to transition to manual control of vehicle 710 based at least in part on situational awareness 920.

Figure 10:
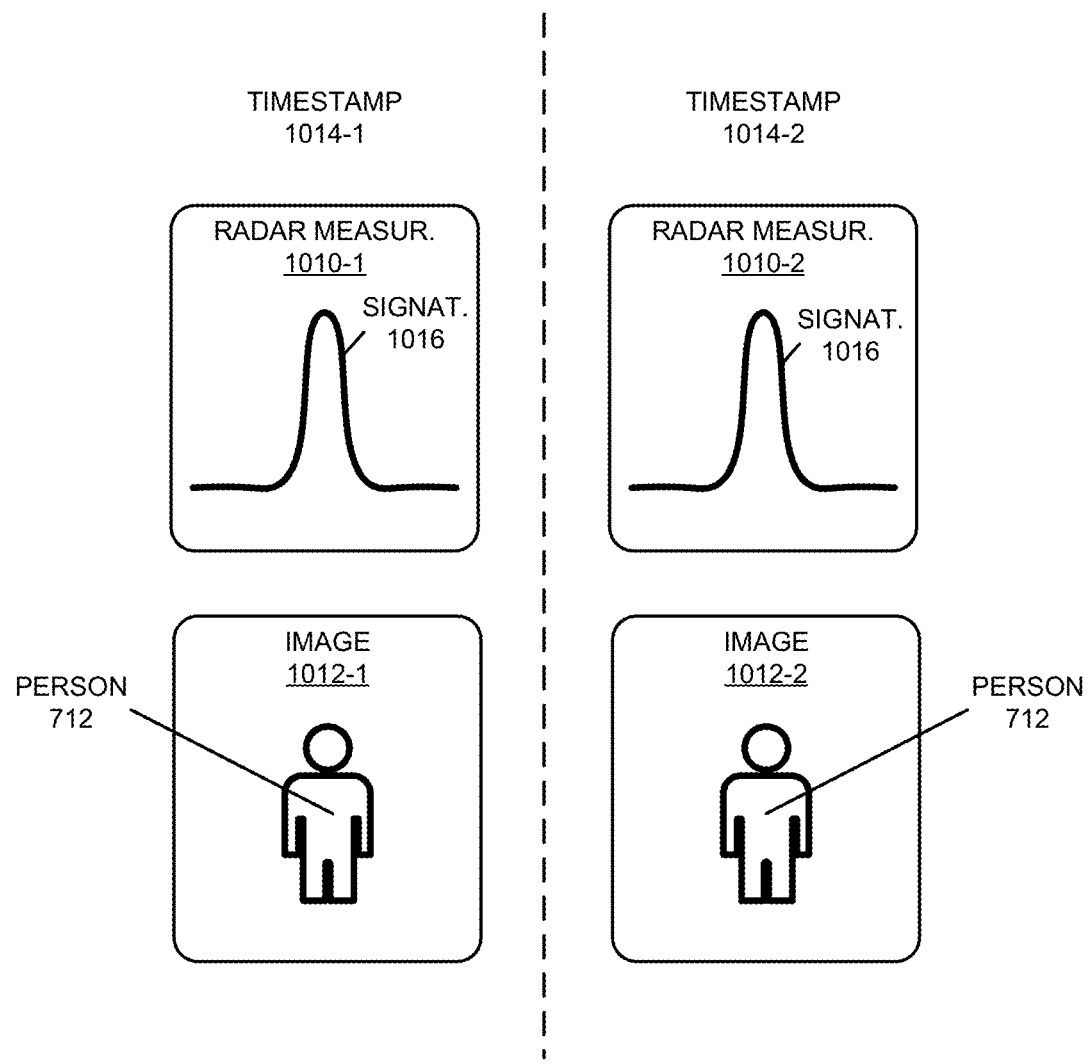
FIG. 10 is a drawing illustrating an example of selective providing a recommendation using, e.g., the electronic device of FIGS. 1 and 2 in accordance with an embodiment of the present disclosure.

FIG. 10 presents a drawing illustrating an example of selective providing a recommendation using electronic device 112 (FIGS. 1 and 2). Notably, sensor(s) may continuously, periodically or as needed, acquire one or more measurements in an environment that is external to electronic device 112 (such as inside of a vehicle), where the one or more measurement provides information associated with a person located in a driver's position in the vehicle, and the one or more measurements includes a non-contact measurement. For example, the one or more measurements may include one or more instances radar measurements 1010 and one or more instances optical measurement (such as capturing images 1012), such as a sequence of measurements at timestamps 1014. Then, electronic device 112 may analyze the radar measurements 1010 to extract a signature 1016 associated with the person and/or to determine a vital sign (such as a pulse and/or a respiration rate). Moreover, electronic device 112 may analyze image 1012 to determine a physiological state and/or an inferred emotional state of the person. In general, the information provided by the one or more measurements may be compared or jointly analyzed.

Next, electronic device 112 may use the one or more measurements to asses situational awareness of a potential driver. The situational awareness may include a physiological state and/or an inferred emotional state of the person. For example, the physiological state may include: an awake state, an alert state, and/or an oriented state. Thus, if a potential driver is drowsy, sleeping, distracted, drunk, panicked (e.g., overwhelmed by fear) and/or angry, they are not capable of safely assuming control of a vehicle.

Alternatively or additionally, the physiological state may include a vital sign of the person. For example, if the person is situationally aware and they perceive that there is a risk of an accident based on the current driving condition(s) associated with operation of the vehicle, they may be afraid. This fear is appropriate to the circumstances (i.e., they should be afraid) and may result in an associated physiological response, such as a sudden increase in the heart or pulse rate and/or respiration (e.g., an increase of 5%, 10%, 20% or more with a 3-10 seconds). Therefore, the physiological state may include a change in the vital sign corresponding to a change in a driving condition associated with operation of the vehicle. When this change is detected, electronic device 112 may conclude that the person is situationally aware.

Thus, if there is a potentially dangerous situation, which is leads the partial or fully autonomous vehicle application to provide the request, and the person reacts in a manner indicative of fear or alarm (but not panic, so that the person is capable of responding to the current driving circumstances), they may be situationally aware and capable of assuming effective manual control. In this way, the feedback techniques may help ensure that a transition to manual control of the vehicle occurs when it is likely to be positive or constructive as a safety measure or failsafe. Consequently, the feedback techniques may help reduce an accident rate and/or improve a safety performance of self-driving technology.

While the preceding example illustrated the use of the feedback techniques in an automobile, in other embodiments the feedback techniques may be used in a wide variety of vehicles that use a partial or fully autonomous vehicle application (e.g., an autopilot), such as an airplane, a ship, etc.

In other embodiments of the feedback techniques, electronic device 112 may be used within a vehicle to facilitate automation of environmental control. Notably, instead of attempting to regulate an environmental condition according to a predefined setpoint (such as maintaining a desired temperature), electronic device 112 may be used to automatically adjust an environmental condition based at least in part on the perceptions of one or more persons in the environment.

Figure 11:
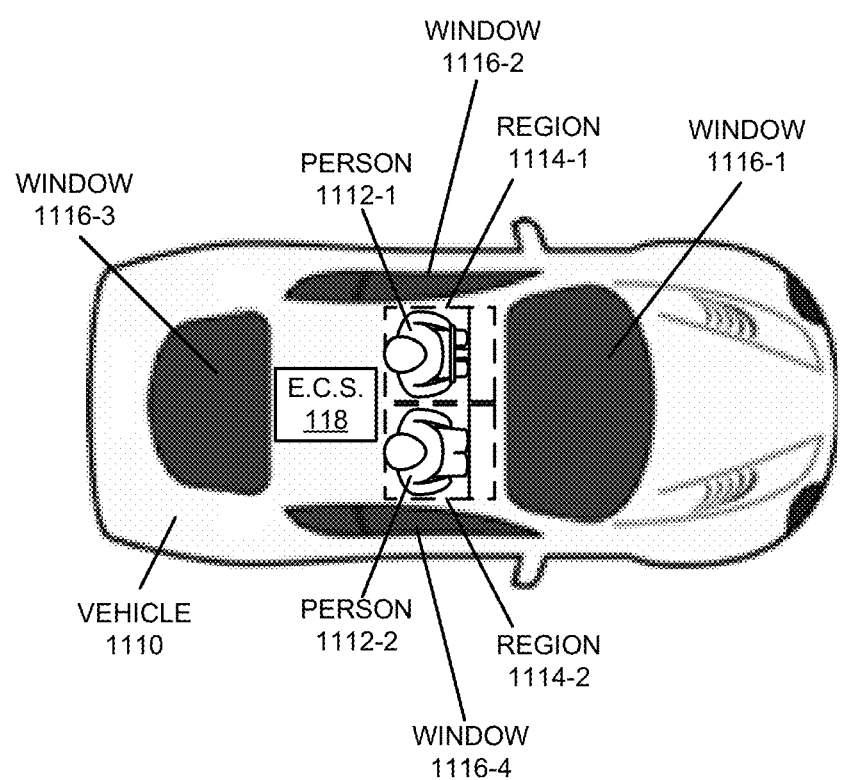
FIG. 11 is a drawing illustrating an example of an environment within a vehicle in accordance with an embodiment of the present disclosure.

FIG. 11 presents a drawing illustrating an example of an environment within a vehicle 1110. Notably, there may be one or more persons 1112 at different portions or regions 1114 in the environment. Moreover, there may be one or more barriers at a periphery of the environment, such as windows 1116. An environmental control system (E.C.S.) 1118 in vehicle 1110 may maintain one or more environmental conditions in the environment, such as the temperature, relative humidity, and/or visibility through one or more of windows 1116. Embodiments of the feedback techniques may be used to assist environmental control system 1118, such as by automating modifications to one or more environmental controls or one or more environmental control settings.

Figure 12:
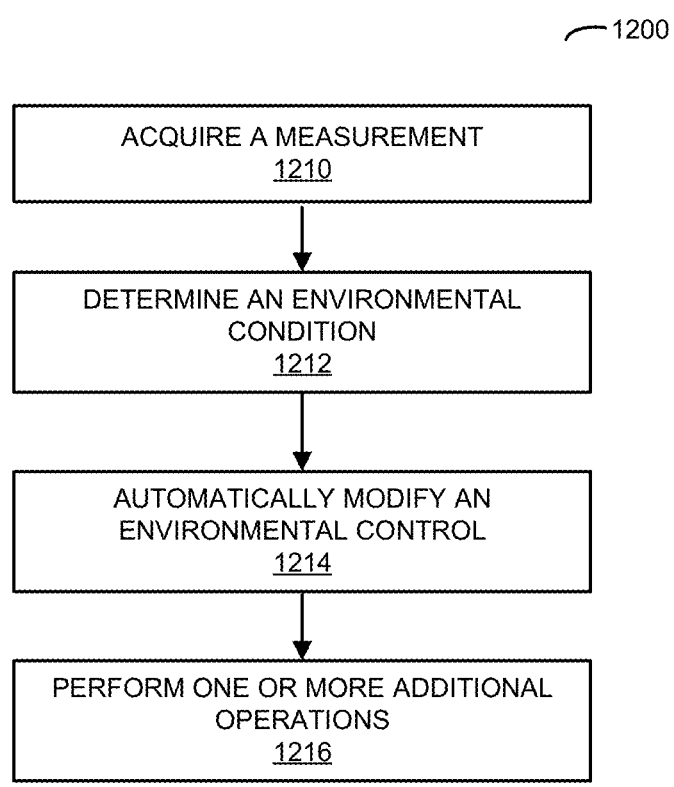
FIG. 12 is a flow diagram illustrating an example of a method for automatically modifying an environmental control in accordance with an embodiment of the present disclosure.

This is shown in FIG. 12, which presents a flow diagram illustrating an example of a method 1200 for automatically modifying an environmental control. This method may be performed by an electronic device (such as electronic device 112 in FIGS. 1 and 2) or a component in the electronic device (such as an integrated circuit or a processor). During operation, the electronic device may acquire, using one or more sensors, a measurement (operation 1210) within an environment that is external to the electronic device, where the measurement includes a non-contact measurement associated with a window or one or more biological lifeforms in the environment. Note that the one or more sensors may include: a transmitter that transmits wireless signals and a receiver that receives wireless-return signals; and/or an image sensor. Alternatively or additionally, the one or more sensors may include an image sensor that performs optical measurements (such as capturing one or more images or a video).

Then, the electronic device may determine an environmental condition (operation 1212) based at least in part on the measurement.

Next, the electronic device may automatically modify the environmental control (operation 1214) associated with the environment based at least in part on the environmental condition. Note that modifying the environmental control may include changing one or more of: a thermostat setting (such as a temperature setpoint), a fan setting (such as on or off, a blower speed, etc.), a fan direction (such as directing an air flow onto a window), a state of a seat heater (such as on or off, an amount of heating, etc.), a state of seat cooling (such as on or off, an amount of seat cooling, etc.), a state of air conditioning (such as on or off, an amount of air conditioning, etc.), a windshield wiper state (such as on or off, a windshield wiper speed, etc., e.g., when the environmental condition indicates that the biological lifeform is having difficulty seeing through the window), a state of a defrost or defogging circuit (such as on or off), etc.

For example, the environmental condition may include presence of ice on a first surface of the window, and the environmental control may activate de-icing of the first surface of the window. Alternatively or additionally, the environmental condition may include presence of condensed water vapor on a second surface of the window, and the environmental control may activate air conditioning and may increase and/or direct airflow onto the second surface or may activate a defrost or defogging circuit.

Furthermore, the environmental condition may include perception of temperature in the environment by a biological lifeform in the environment, and the environment control may adapt a temperature in at least a portion of the environment that includes the biological lifeform. In some embodiments, the electronic device may determine or estimate the perception based at least in part on: a behavior of the biological lifeform and/or an inferred emotional state of the biological lifeform.

Additionally, the environmental condition may include different perceptions of temperature in the environment by a first biological lifeform and a second biological lifeform in the environment, the environment control may adapt a first temperature in a first portion of the environment that include the first biological lifeform and may adapt a second temperature in a second portion of the environment that include the second biological lifeform, and the first temperature may be different from the second temperature. In some embodiments, adapting a given temperature may include: changing one or more of: a thermostat setting, a fan setting, a fan direction, a state of a seat heater, a state of seat cooling, a state of air conditioning, a windshield wiper state, a state of a defrost or defogging circuit, etc.

Note that the environmental condition may include detecting a presence of a biological lifeform in a region in the environment. Thus, the environmental control may be automatically modified when a person is detected in, e.g., a passenger seat in a car.

In some embodiments, the electronic device performs one or more optional additional operations (operation 1216).

Note that the electronic device may be a portable or removable electronic device, such as a measurement or sensor module that is installed in or integrated into the vehicle.

In some embodiments of method 400 (400), 800 (FIG. 8) and/or 1200 there may be additional or fewer operations. Moreover, the order of the operations may be changed, and/or two or more operations may be combined into a single operation.

Figure 13:
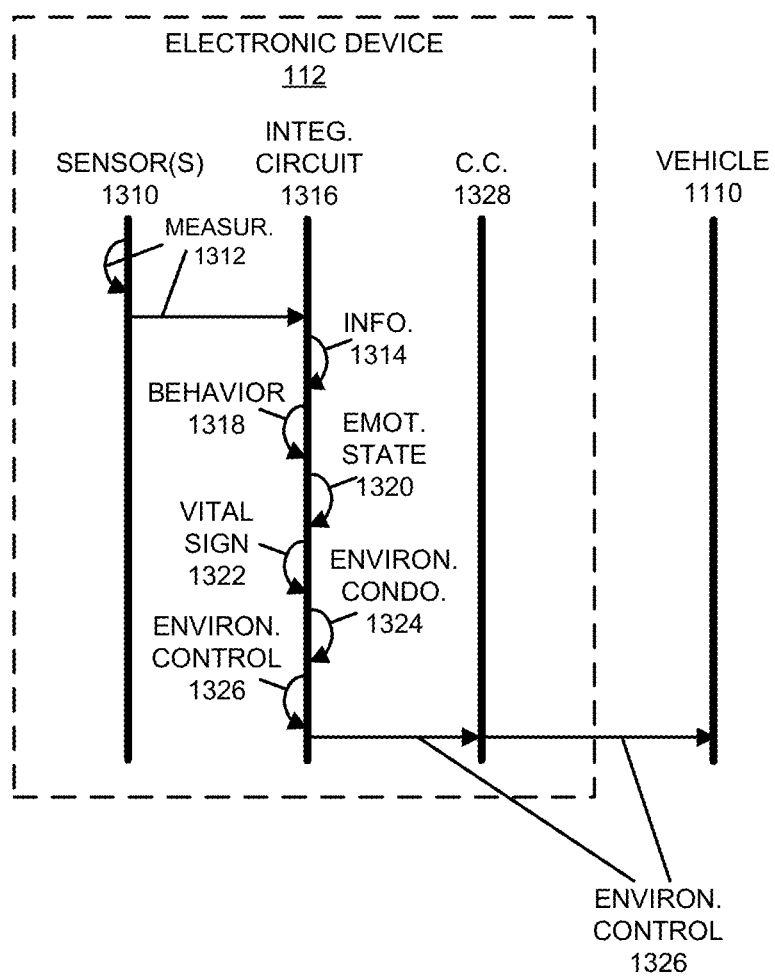
FIG. 13 is a drawing illustrating an example of communication among components, e.g., in the electronic device of FIGS. 1 and 2 in accordance with an embodiment of the present disclosure.

FIG. 13 presents a drawing illustrating an example of communication among components in electronic device 112 and vehicle 1110. Notably, sensor(s) 1310 in electronic device 112 may acquire one or more measurements 1312 in an environment that is external to electronic device 112, where the one or more measurements 1312 provide information 1314 associated with a window or one or more biological lifeforms (such as one or more people or one or more animals) in the environment, and the one or more measurements 1312 include a non-contact measurement.

Then, an integrated circuit (I.C.) 1316 in electronic device 112 may extract information 1314 based at least in part on the one or more measurements 1312, and may determine an environmental condition 1324 based at least in part on the one or more measurements 1312 and/or information 1314. For example, environmental condition 1324 may include perception of temperature in the environment by a biological lifeform in the environment (such as that the temperature is too cold or feels too cold). In some embodiments, integrated circuit 1316 may determine or estimate the perception based at least in part on: a behavior 1318 of the biological lifeform (such as shivering, folding or wrapping their arms around their torso, a sound made by a person, e.g., 'brrrr', stating that they are warm or cold, non-verbal communication, a facial expression, etc.), an inferred emotional state 1320 of the biological lifeform and/or a vital sign 1322 of the biological lifeform.

Next, integrated circuit 1316 may automatically modify environmental control 1326 associated with the environment based at least in part on environmental condition 1324. For example, integrated circuit 1316 may provide the modified environmental control 1326 to communication circuit 1328 in electronic device 112, which provides the modified environmental control 1326 to vehicle 1110. In response, vehicle 1110 may change one or more of: a thermostat setting, a fan setting, a fan direction, a state of a seat heater, a state of seat cooling, a state of air conditioning, a windshield wiper state, a defrost or defogging circuit, etc. Thus, in response to a biological lifeform perceiving that the temperature in the environment is too cold or feels too cold, the modified environment control 1326 may adapt a temperature in at least a portion of the environment in vehicle 1110 that includes the biological lifeform.

While communication between the components in FIGS. 5, 9 and/or 13 is illustrated with unilateral or bilateral communication (e.g., lines having a single arrow or dual arrows), in general a given communication operation may be unilateral or bilateral.

Figure 14:
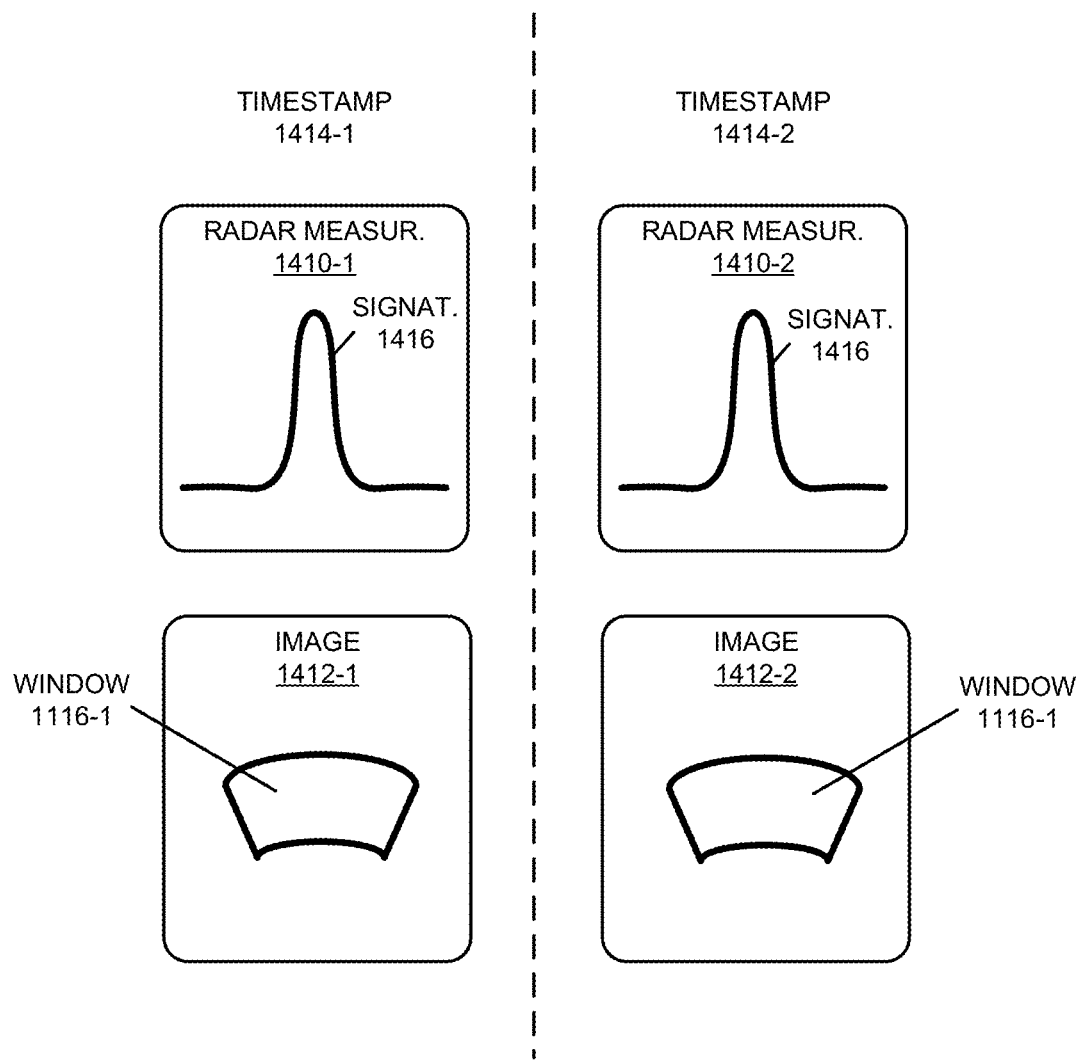
FIG. 14 is a drawing illustrating an example of automatically modifying an environmental control using, e.g., the electronic device of FIGS. 1 and 2 in accordance with an embodiment of the present disclosure.

FIG. 14 presents a drawing illustrating an example of automatically modifying an environmental control using electronic device 112 (FIGS. 1 and 2). Notably, sensor(s) may continuously, periodically or as needed, acquire one or more measurements in an environment that is external to electronic device 112 (such as inside of a vehicle), where the one or more measurements include a non-contact measurement associated with a window or one or more biological lifeforms in the environment (such as one or more people and/or an animal, e.g., a pet). For example, the one or more measurements may include radar measurements 1410 and/or an optical measurement (such as capturing an image 1412) at different timestamps 1414.

Then, electronic device 112 may analyze the radar measurements 1410 to extract a signature 1416 associated with the window or the one or more biological lifeforms, and then may determine a classification or an occurrence of an environmental condition based at least in part on signature 1416. Alternatively or additionally, electronic device may analyze the image to determine the classification or the occurrence of the environmental condition based at least in part on the information included in image 1412. For example, electronic device 112 may detect the presence of ice, fog, moisture or condensation (such as condensed water vapor) on an interior or an exterior surface of the window.

Furthermore, the environmental condition may include perception of temperature in the environment by a person in the environment. Notably, the perception may be determined or estimated based at least in part on: a behavior of the person and/or an inferred emotional state of the person. For example, the behavior may include shivering, folded arms, verbal complaining, a facial expression, etc., that indicates that the person feels cold (regardless of the actual temperature around the person in one of regions 1114 in FIG. 11). Alternatively or additionally, the behavior may include sweating (such as the presence of sweat on a person's skin or their clothing may be soaked), the person may be fanning themselves, verbal complaining, a facial expression, etc., that indicates that the person feels hot (regardless of the actual temperature around the person in one of regions 1114 in FIG. 11). In some embodiments, the behavior may include squinting or wiping away moisture or condensed water vapor from a portion of a window, which may indicate that the person is having difficulty seeing through the window. Additionally, the emotional state may include irritation. In these and other embodiments in the present disclosure, an emotional state may be estimated by using the one or more measurements as inputs to a pretrained neural network or a machine-learning model that outputs an estimate of an emotional state (such as a probability of a particular emotional state or a classification in a particular emotional state).

Based on the determined environmental condition, electronic device 112 may automatically modify the environmental control or may provide an instruction to an environmental control system. When the environmental condition involves perception of temperature, this modification may adjust a temperature in at least one of regions 1114 (FIG. 11) by changing one or more of: a temperature setpoint, a fan setting, a state of a seat heater, a state of seat heating, a state of air conditioning, etc. Alternatively, when the environmental condition involves a condition related to a window, the modification may adjust one or more of: a windshield wiper state, a state of a defrost or defogging circuit, a state of air conditioning, a fan setting, a fan direction, etc. Note that in the present discussion a 'state' may include: on, off, a real value corresponding to an amount between a minimum or a maximum amount, etc.

While the preceding example illustrated the use of the feedback techniques in an automobile, in other embodiments the feedback techniques may be used in a wide variety of vehicles or environments that include an environmental control system, such as an airplane, a ship, an office, a room, a building, etc.

Figure 15:
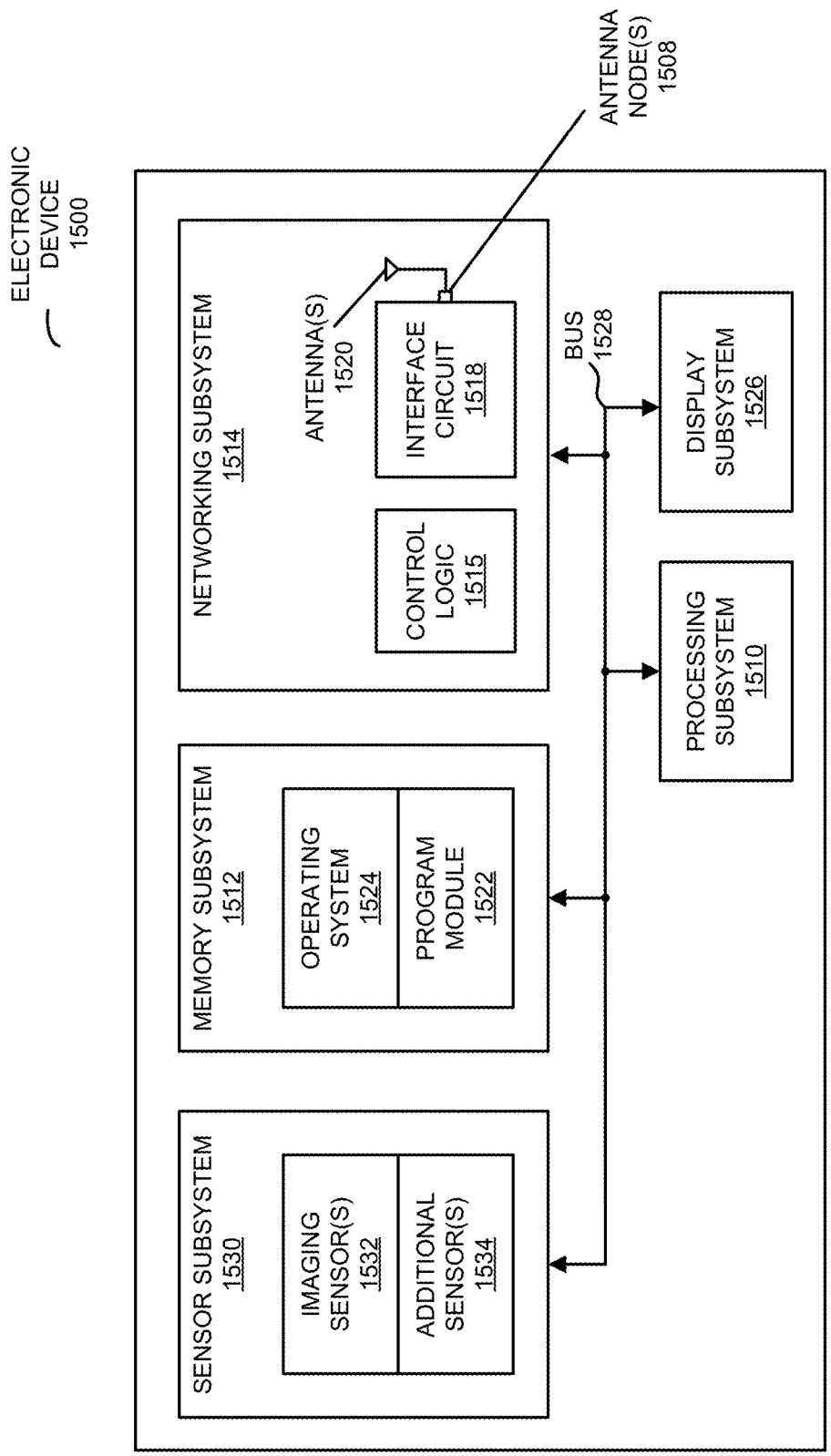
FIG. 15 is a block diagram illustrating an example of an electronic device in accordance with an embodiment of the present disclosure.

We now describe embodiments of an electronic device, which may perform at least some of the operations in the security and/or the feedback techniques. FIG. 15 presents a block diagram illustrating an example of an electronic device 1500, such as electronic device 112 (FIGS. 1 and 2). This electronic device may include processing subsystem 1510, memory subsystem 1512, networking subsystem 1514 and sensor subsystem 1530. Processing subsystem 1510 includes one or more devices configured to perform computational operations. For example, processing subsystem 1510 can include one or more microprocessors, ASICs, microcontrollers, programmable-logic devices, graphical processor units (GPUs) and/or one or more digital signal processors (DSPs).

Memory subsystem 1512 includes one or more devices for storing data and/or instructions for processing subsystem 1510 and networking subsystem 1514. For example, memory subsystem 1512 can include dynamic random access memory (DRAM), static random access memory (SRAM), and/or other types of memory (which collectively or individually are sometimes referred to as a 'computer-readable storage medium'). In some embodiments, instructions for processing subsystem 1510 in memory subsystem 1512 include: one or more program modules or sets of instructions (such as program instructions 1522 or operating system 1524), which may be executed by processing subsystem 1510. Note that the one or more computer programs may constitute a computer-program mechanism. Moreover, instructions in the various modules in memory subsystem 1512 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 1510.

In addition, memory subsystem 1512 can include mechanisms for controlling access to the memory. In some embodiments, memory subsystem 1512 includes a memory hierarchy that comprises one or more caches coupled to memory in electronic device 1500. In some of these embodiments, one or more of the caches is located in processing subsystem 1510.

In some embodiments, memory subsystem 1512 is coupled to one or more high-capacity mass-storage devices (not shown). For example, memory subsystem 1512 can be coupled to a magnetic or optical drive, a solid-state drive, or another type of mass-storage device. In these embodiments, memory subsystem 1512 can be used by electronic device 1500 as fast-access storage for often-used data, while the mass-storage device is used to store less frequently used data.

Networking subsystem 1514 includes one or more devices configured to couple to and communicate on a wired and/or wireless network (i.e., to perform network operations), including: control logic 1516, an interface circuit 1518 and one or more antennas 1520 (or antenna elements). (While FIG. 15 includes one or more antennas 1520, in some embodiments electronic device 1500 includes one or more nodes, such as nodes 1508, e.g., a pad, which can be coupled to the one or more antennas 1520. Thus, electronic device 1500 may or may not include the one or more antennas 1520.) For example, networking subsystem 1514 can include a Bluetooth networking system, a cellular networking system (e.g., a 3G/4G/5G network such as UMTS, LTE, etc.), a USB networking system, a networking system based on the standards described in IEEE 802.11 (e.g., a Wi-Fi networking system), an Ethernet networking system, and/or another networking system.

Note that a transmit or receive antenna pattern (or antenna radiation pattern) of electronic device 1500 may be adapted or changed using pattern shapers (such as reflectors) in one or more antennas 1520 (or antenna elements), which can be independently and selectively electrically coupled to ground to steer the transmit antenna pattern in different directions. (Alternatively or additionally, the transmit or receive antenna pattern may be adapted or changed using a phased array.) Thus, if one or more antennas 1520 include N antenna pattern shapers, the one or more antennas may have $2^N$ different antenna pattern configurations. More generally, a given antenna pattern may include amplitudes and/or phases of signals that specify a direction of the main or primary lobe of the given antenna pattern, as well as so-called 'exclusion regions' or 'exclusion zones' (which are sometimes referred to as 'notches' or 'nulls'). Note that an exclusion zone of the given antenna pattern includes a low-intensity region of the given antenna pattern. While the intensity is not necessarily zero in the exclusion zone, it may be below a threshold, such as 3 dB or lower than the peak gain of the given antenna pattern. Thus, the given antenna pattern may include a local maximum (e.g., a primary beam) that directs gain in the direction of electronic device 1500 that is of interest, and one or more local minima that reduce gain in the direction of other electronic devices that are not of interest. In this way, the given antenna pattern may be selected, e.g., to target an object of interest in an environment of electronic device 1500.

Networking subsystem 1514 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' or a 'connection' between the electronic devices does not yet exist. Therefore, electronic device 1500 may use the mechanisms in networking subsystem 1514 for performing simple wireless communication between the electronic devices, e.g., transmitting frames and/or scanning for frames transmitted by other electronic devices.

Within electronic device 1500, processing subsystem 1510, memory subsystem 1512, and networking subsystem 1514 are coupled together using bus 1528. Bus 1528 may include an electrical, optical, and/or electro-optical connection that the subsystems can use to communicate commands and data among one another. Although only one bus 1528 is shown for clarity, different embodiments can include a different number or configuration of electrical, optical, and/or electro-optical connections among the subsystems.

In some embodiments, electronic device 1500 includes an optional display subsystem 1526 for displaying information on a display, which may include a display driver and the display, such as a liquid-crystal display, a multi-touch touchscreen, etc.

Furthermore, electronic device 1500 may include a sensor subsystem 1530, which may include one or more radar sensors 1532 with one or more transmitters, one or more receivers, one or more sets of transmit antennas and one or more sets of receive antennas that perform MIMO radar measurements. In some embodiments, sensor subsystem 1530 includes one or more image sensors that acquire images (such as a CCD or a CMOS sensor) and/or one or more additional sensors 1534 (such as a light-intensity sensor, radar, sonar, lidar, etc.). These other or additional sensors may be used separately or in conjunction with the one or more radar sensors 1532.

Electronic device 1500 can be (or can be included in) a wide variety of electronic devices. For example, electronic device 1500 can be (or can be included in): a desktop computer, a laptop computer, a subnotebook/netbook, a server, a computer, a mainframe computer, a cloud-based computer, a tablet computer, a smartphone, a cellular telephone, a smartwatch, a consumer-electronic device, a portable computing device, a transceiver, a measurement device, another electronic device and/or a vehicle.

Although specific components are used to describe electronic device 1500, in alternative embodiments, different components and/or subsystems may be present in electronic device 1500. For example, electronic device 1500 may include one or more additional processing subsystems, memory subsystems, networking subsystems, display subsystems and/or sensor subsystems. Additionally, one or more of the subsystems may not be present in electronic device 1500. Moreover, in some embodiments, electronic device 1500 may include one or more additional subsystems that are not shown in FIG. 15. Also, although separate subsystems are shown in FIG. 15, in some embodiments some or all of a given subsystem or component can be integrated into one or more of the other subsystems or component(s) in electronic device 1500. For example, in some embodiments program instructions 1522 are included in operating system 1524 and/or control logic 1516 is included in interface circuit 1518.

Moreover, the circuits and components in electronic device 1500 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit (which is sometimes referred to as a 'communication circuit' or a 'means for communication') may implement some or all of the functionality of networking subsystem 1514 or sensor subsystem 1530. The integrated circuit may include hardware and/or software mechanisms that are used for transmitting wireless or radar signals from electronic device 1500 and receiving wireless or radar signals at electronic device 1500 from other electronic devices. Aside from the mechanisms herein described, radios are generally known in the art and hence are not described in detail. In general, networking subsystem 1514 and/or the integrated circuit can include any number of radios. Note that the radios in multiple-radio embodiments function in a similar way to the described single-radio embodiments.

In some embodiments, networking subsystem 1514 and/or the integrated circuit include a configuration mechanism (such as one or more hardware and/or software mechanisms) that configures the radio(s) to transmit and/or receive on a given communication channel (e.g., a given carrier frequency). For example, in some embodiments, the configuration mechanism can be used to switch the radio from monitoring and/or transmitting on a given communication channel to monitoring and/or transmitting on a different communication channel. (Note that 'monitoring' as used herein comprises receiving signals from other electronic devices and possibly performing one or more processing operations on the received signals)

Moreover, another integrated circuit may implement some or all of the functionality related to the security and/or the feedback techniques.

In some embodiments, an output of a process for designing a given integrated circuit, or a portion of the given integrated circuit, which includes one or more of the circuits described herein may be a computer-readable medium such as, for example, a magnetic tape or an optical or magnetic disk. The computer-readable medium may be encoded with data structures or other information describing circuitry that may be physically instantiated as the given integrated circuit or the portion of the given integrated circuit. Although various formats may be used for such encoding, these data structures are commonly written in: Caltech Intermediate Format (CIF), Calma GDS II Stream Format (GDSII) or Electronic Design Interchange Format (EDIF). Those of skill in the art of integrated circuit design can develop such data structures from schematics of the type detailed above and the corresponding descriptions and encode the data structures on the computer-readable medium. Those of skill in the art of integrated circuit fabrication can use such encoded data to fabricate integrated circuits that include one or more of the circuits described herein.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the security or the feedback techniques may be implemented using program instructions 1522, operating system 1524 (such as a driver for interface circuit 1518) or in firmware in interface circuit 1518. Alternatively or additionally, at least some of the operations in the security or the feedback techniques may be implemented in a physical layer, such as hardware in interface circuit 1518 or sensor subsystem 1530.

While the preceding embodiments illustrated the use of a vehicle, such as a car, a truck, a bus, etc., in other embodiments the security and/or the feedback techniques are used in conjunction with a flying vehicle (such as a drone, a helicopter, an airplane, etc.), a boat or a ship, and/or a submersible vehicle (such as a drone or a submarine).

In the preceding description, we refer to 'some embodiments.' Note that 'some embodiments' describes a subset of all of the possible embodiments, but does not always specify the same subset of embodiments. Note that numerical values in the preceding embodiments are illustrative examples of some embodiments. In other embodiments of the security or the feedback techniques, different numerical values may be used.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. An electronic device, comprising:
   one or more sensors;
   an integrated circuit, coupled to the one or more sensors, configured to:
      acquire, using the one or more sensors, a measurement within an environment that is external to the electronic device, wherein the measurement provides information associated with a person located in a driver's position in a vehicle, and wherein the measurement comprises a non-contact measurement;
      assess situational awareness of the person based at least in part on the measurement and a change in a vital sign of the person corresponding to a change in a driving condition associated with operation of the vehicle;
      receive a request associated with a partial or fully autonomous vehicle application to transition to manual control of the vehicle; and
      selectively provide a recommendation to the partial or fully autonomous vehicle application to transition to manual control of the vehicle based at least in part on the request and the situational awareness.

2. The electronic device of claim 1, wherein the one or more sensors comprises a transmitter configured to transmit wireless signals and a receiver configured to receive wireless-return signals.

3. The electronic device of claim 1, wherein the request corresponds to an occurrence of an unknown or an unsafe driving condition associated with operation of the vehicle.

4. The electronic device of claim 1, wherein the situational awareness indicates an awareness of the person of to a current driving condition associated with operation of the vehicle.

5. The electronic device of claim 1, wherein the situational awareness comprises a physiological state or an inferred emotional state of the person.

6. The electronic device of claim 5, wherein the physiological state comprises an awake state, an alert state, or an oriented state.

7. The electronic device of claim 1, wherein, when the recommendation is not provided, the integrated circuit is configured to selectively provide a second recommendation to the partial or fully autonomous vehicle application to not transition to manual control of the vehicle based at least in part on the request and the situational awareness.

8. A vehicle, comprising:
one or more sensors;
an integrated circuit, coupled to the one or more sensors, configured to:
acquire, using the one or more sensors, a measurement within an environment that is external to the electronic device, wherein the measurement provides information associated with a person located in a driver's position in a vehicle, and wherein the measurement comprises a non-contact measurement;
assess situational awareness of the person based at least in part on the measurement and a change in a vital sign of the person corresponding to a change in a driving condition associated with operation of the vehicle;
receive a request associated with a partial or fully autonomous vehicle application to transition to manual control of the vehicle; and
selectively provide a recommendation to the partial or fully autonomous vehicle application to transition to manual control of the vehicle based at least in part on the request and the situational awareness.

9. The vehicle of claim 8, wherein the situational awareness comprises a physiological state or an inferred emotional state of the person.

10. The vehicle of claim 9, wherein the physiological state comprises an awake state, an alert state, or an oriented state.

11. The vehicle of claim 8, wherein the situational awareness indicates an awareness of the person of to a current driving condition associated with operation of the vehicle.

12. A non-transitory computer-readable storage medium for use in conjunction with an electronic device, the computer-readable storage medium storing program instructions, wherein, when executed by the computer system, the program instructions cause the computer system to perform one or more operations comprising:
acquiring, using one or more sensors, a measurement within an environment that is external to the electronic device, wherein the measurement provides information associated with a person located in a driver's position in a vehicle, and wherein the measurement comprises a non-contact measurement;
assessing situational awareness of the person based at least in part on the measurement and a change in a vital sign of the person corresponding to a change in a driving condition associated with operation of the vehicle;
receiving a request associated with a partial or fully autonomous vehicle application to transition to manual control of the vehicle; and
selectively providing a recommendation to the partial or fully autonomous vehicle application to transition to manual control of the vehicle based at least in part on the request and the situational awareness.

13. The non-transitory computer-readable storage medium of claim 12, wherein the situational awareness comprises a physiological state or an inferred emotional state of the person.

14. The non-transitory computer-readable storage medium of claim 13, wherein the physiological state comprises an awake state, an alert state, or an oriented state.

15. The non-transitory computer-readable storage medium of claim 12, wherein the situational awareness indicates an awareness of the person of to a current driving condition associated with operation of the vehicle.

16. A method for selectively providing a recommendation, comprising:
by an electronic device:
acquiring, using one or more sensors, a measurement within an environment that is external to the electronic device, wherein the measurement provides information associated with a person located in a driver's position in a vehicle, and wherein the measurement comprises a non-contact measurement;
assessing situational awareness of the person based at least in part on the measurement and a change in a vital sign of the person corresponding to a change in a driving condition associated with operation of the vehicle;
receiving a request associated with a partial or fully autonomous vehicle application to transition to manual control of the vehicle; and
selectively providing the recommendation to the partial or fully autonomous vehicle application to transition to manual control of the vehicle based at least in part on the request and the situational awareness.

17. The method of claim 16, wherein the situational awareness comprises a physiological state or an inferred emotional state of the person.

18. The method of claim 17, wherein the an awake state, an alert state, or an oriented state.

19. The method of claim 16, wherein the situational awareness indicates an awareness of the person of to a current driving condition associated with operation of the vehicle.

20. The method of claim 16, wherein, when the recommendation is not provided, the method comprises selectively providing a second recommendation to the partial or fully autonomous vehicle application to not transition to manual control of the vehicle based at least in part on the request and the situational awareness.

* * * * *